United States Patent [19]

Hayasaka et al.

[11] Patent Number: 5,723,075
[45] Date of Patent: Mar. 3, 1998

[54] DIMERIZED THIOUREA DERIVATIVES NEAR-INFARED ABSORBENTS COMPRISING THE SAME, AND HEAT WAVE SHIELDING MATERIALS COMPRISING THE SAME

[75] Inventors: Hideki Hayasaka; Toshiyuki Takano; Toshimi Satake, all of Tokyo, Japan

[73] Assignee: Nippon Paper Industries Co., Ltd., Tokyo, Japan

[21] Appl. No.: 634,126

[22] Filed: Apr. 19, 1996

Related U.S. Application Data

[63] Continuation of Ser. No. 197,948, Feb. 17, 1994, abandoned.

[30] Foreign Application Priority Data

| Feb. 19, 1993 | [JP] | Japan | 5-030954 |
| Aug. 11, 1993 | [JP] | Japan | 5-199664 |

[51] Int. Cl.$^6$ .................. F21V 9/04; C07C 303/00; C07C 335/00
[52] U.S. Cl. .................. 252/587; 564/23; 564/26; 564/27; 564/29
[58] Field of Search .................. 252/587; 564/23, 564/26, 27, 29

[56] References Cited

U.S. PATENT DOCUMENTS

| 3,165,510 | 1/1965 | Hoenen et al. |  |
| 3,856,847 | 12/1974 | Kohmoto et al. | 564/26 |
| 4,020,095 | 4/1977 | Noguchi et al. |  |
| 4,112,100 | 9/1978 | Callahan et al. |  |
| 4,438,135 | 3/1984 | Chow . |  |
| 5,236,633 | 8/1993 | Satake et al. |  |
| 5,354,514 | 10/1994 | Satake et al. | 252/587 |

FOREIGN PATENT DOCUMENTS

| 0346772 | 6/1989 | European Pat. Off. |
| 1489M | 9/1962 | France . |
| 898896 | 10/1953 | Germany . |
| 1134889 | 11/1968 | United Kingdom . |

OTHER PUBLICATIONS

Gupta et al., Indian Journal of Chemistry, vol. 18B, No. 4, pp. 381–382, (1979).
Sarkis et al., J. Heterocyclic Chem., vol. 22, pp. 137–140, (1985).
Hirayama et al., Chemical Abstracts 95: 35421 Abstract of Yakugaku Zasshi, vol. 100, No. 12, pp. 1225–1234, (1980).
Chemical Abstracts, vol. 55, No. 23, Nov. 13, 1961, abstract No. 23419f.
Achiv. Der Pharmazie, vol. 296, No. 10, Oct. 1963, pp. 641–650.
Chemical Abstracts, vol. 70, No. 7, Feb. 1969, abstract No. 27511z.

(List continued on next page.)

*Primary Examiner*—Philip Tucker
*Attorney, Agent, or Firm*—Sherman and Shalloway

[57] ABSTRACT

A near-infrared absorbent is obtained by heating a dimerized thiourea derivative of Formula [1] or [2] and a copper compound:

$$R-NH-\underset{\underset{S}{\|}}{C}-NH-\underset{R_5}{\overset{R_1}{\bigcirc}}\underset{R_6}{\overset{R_2}{-}}A-\underset{R_7}{\overset{R_3}{\bigcirc}}\underset{R_8}{\overset{R_4}{-}}NH-\underset{\underset{S}{\|}}{C}-NH-R \quad [1]$$

$$R-NH-\underset{\underset{S}{\|}}{C}-NH-B-NH-\underset{\underset{S}{\|}}{C}-NH-R \quad [2]$$

The near-infrared absorbent is used to obtain a near-infrared absorbent resin material having a wide absorption in the near-infrared region, and the absorbent does not substantially decompose at a molding temperature of the resin. Typical examples of the dimerized thiourea derivative are 4,4'-di(benzylthiocarbamoyl)-aminodiphenylmethane, 4,4'-di(benzylthiocarbamoyl)-aminodiphenylhexafluoropropane, and 1,4'-di(dibenzoylthiocarbamoylamino)-2,5-dimethylbenzene, and typical examples of the copper compound are copper stearate and copper β-acryloyloxypropylhydrogenphthalate.

32 Claims, 7 Drawing Sheets

OTHER PUBLICATIONS

Indian Journal of Chemistry, Section B, vol. 18B, No. 4, 1979, pp. 381–382.

Arzneimittel–Forschung, vol. 17, No. 4, 1969, pp. 425–431.

Die Pharmazie, vol. 48, No. 6, Jun.1993, pp. 414–417.

Chemical Abstracts, vol. 95, No. 5, Aug. 3, 1981, abstract No. 35421b.

Journal of the Chemical Society (C), No. 21, 1967, pp. 2212–2270.

Chemical Abstracts, vol. 70, no. 19, May 12, 1969, abstract No. 871809.

Chemical Abstracts, vol. 69, No. 7, Aug. 12, 1968, abstract No. 26886t.

Bioconjugate Chemistry, vol. 2, No. 4, 1991, pp. 232–241.

Biologia Plantarum, vol. 15, No. 5, 1973, pp. 318–323.

Chemical Abstracts, vol. 92, No. 13, Mar. 1980, abstract No. 1106345.

Chemical Abstracts, vol. 108, No. 17, Apr. 25, 1988, abstract No. 150356h.

Journal of Medicinal Chemistry, vol. 35, No. 2, Jan. 24, 1992, pp. 1826–1828.

Journal of Organic Chemistry of the USSR, vol. 27, No. 10, Mar. 10, 1992, pp. 1826–1828.

Chemical and Pharmaceutical Bulletin, vol. 29, No. 2, Feb. 1981, pp. 301–307.

Arzneimittel–Forschung, vol. 27, No. 5, 1977, pp. 950–967.

Chemical Abstracts, vol. 75, No. 1, Jul. 5, 1971, abstract No. 5772m.

Chemical Abstracts, vol. 73, No. 16, Oct. 19, 1970, abstract No. 78125w.

Chemical Abstracts, vol. 80, No. 14, Apr. 8, 1974, abstract No. 71512f.

Bulletin of the Chemical Society of Japan, vol. 40, No. 10, Oct. 1967, pp. 2383–2388.

Doklady Bolgarshio Akademii Nauk, vol. 26, No. 3, 1973, pp. 391–394.

Abstract of Japanese Patent Application No. 63–145262, (1988).

Abstract of Japanese Patent Application No. 63–232075, (1988).

Abstract of Japanese Patent Application No. 63–183329, (1988).

Abstract of Japanese Patent Application No. 2–258636, (1990).

Abstract of Japanese Patent Application No. 63–37187, (1988).

Abstract of Japanese Patent Application No. 3–156516, (1991).

Abstract of Japanese Patent Application No. 59–1409, (1984).

Abstract of Japanese Patent Application No. 58–58894, (1983).

Kawaguchi Chemical Industries Co., Ltd. Jul. 6, 1992, pp. 1–5 and 19–20.

Campbell, et al. Journal of Polymer Science (1962) vol. 62, pp. 379–386.

DIMERIZED THIOUREA DERIVATIVES NEAR-INFARED ABSORBENTS COMPRISING THE SAME, AND HEAT WAVE SHIELDING MATERIALS COMPRISING THE SAME

This application is a continuation of application Ser. No. 08/197,948, filed Feb. 17, 1994 now abandoned.

FIELD OF THE INVENTION

This invention relates to a novel dimerized thiourea derivative, a near-infrared absorbent composition comprising the dimerized thiourea derivative and a copper compound, a near-infrared absorbent obtained by heating the composition, a near-infrared absorbent resin obtained by melting the near-infrared absorbent composition or the near-infrared absorbent, and a heat wave shielding material using the near-infrared absorbent resin.

DESCRIPTION OF THE PRIOR ART

In Japanese Patent Laid-open Publications (Japanese OPI) 2-3493, 2-34682, 2-80486, and 3-246256, the inventors already disclosed a near-infrared absorbent composition comprising a thiourea compound and a copper compound, a near-infrared absorbent material obtained by heating the composition, and a near-infrared absorbent resin molding containing the absorbents in a resin, or a near-infrared absorbent resin molding obtained by mixing the absorbents with a radical polymerization initiator and heating the mixture to polymerize.

These near-infrared absorbents obtained by heating a composition comprising a thiourea compound and a copper compound are inexpensive compared to near-infrared absorbent dyes known in the past, and superior in terms of light fastness and near-infrared absorption range.

However, when containing a composition comprising a prior art thiourea compound and a copper compound in a resin and molding to a pellet or a specified form, the composition tends to undergo partial decomposition due to the molding heat, resulting in gas evolution.

OBJECT OF THE INVENTION

Therefore, a primary object of the present invention is to provide a near-infrared absorbent composition, and a near-infrared absorbent, which, heat molded to produce a near-infrared absorbent resin, do not decompose or generate malodorous gases at the melding temperature, a near-infrared absorbent resin containing these near-infrared absorbent composition and near-infrared absorbent, and a heat wave shielding material comprising the resin.

SUMMARY OF THE INVENTION

The above object is attained by a thiourea compound (hereinafter referred to as "dimerized thiourea compound") which has two thiourea structures (—NH—(C=S)—NH—) in the molecule.

In accordance with the present invention, there is provided a near-infrared absorbent composition comprising a dimerized thiourea compound of Formula [1] or Formula [2] and a copper compound:

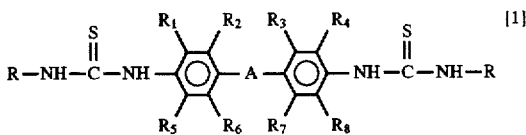

(wherein A denotes $CH_2$, $(CH_2)_2$, S, O, $SO_2$, CONH, NH, or $C(CF_3)_2$. R denotes a substituted or unsubstituted alkyl group having 1 to 18 carbon atoms, a substituted or unsubstituted cycloalkyl group having 3 to 18 carbon atoms, a substituted or unsubstituted aralkyl group having 7 to 30 carbon atoms, a substituted or unsubstituted aryl group having 6 to 30 carbon atoms, a substituted or unsubstituted acyl group having 2 to 20 carbon atoms, a substituted or unsubstituted alkenyl group having 2 to 20 carbon atoms, or a substituted or unsubstituted alkoxycarbonyl group having 2 to 20 carbon atoms. $R_1$, $R_2$, $R_3$, $R_4$, $R_5$, $R_6$, $R_7$, and $R_8$ denote a lower alkyl group having 1 to 6 carbon atoms, lower alkoxy group having 1 to 6 carbon atoms, nitro group, cyano group, halogen atom, or hydrogen atom.)

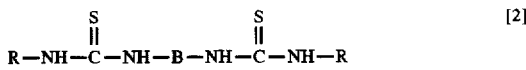

(wherein R denotes the same as R in Formula [1], and B denotes a substituted or unsubstituted benzene ring, naphthalene ring, or biphenyl ring.)

In R of Formula [1] and Formula [2], the alkyl group includes methyl group, ethyl group, n-propyl group, isopropyl group, n-butyl group, sec-butyl group, tert-butyl group, heptyl group, dodecyl group, stearyl group, or the like; the cycloalkyl group includes cyclohexyl group or the like; the aralkyl group includes benzyl group, b-phenylethyl group, or the like; the aryl group includes phenyl group, chlorophenyl group, fluorophenyl group, toluyl group, cyanophenyl group, nitrophenyl group, methoxyphenyl group, 1-naphthyl group, or the like; the acyl group includes benzoyl group or the like, the alkenyl group includes allyl group, 2-butenyl group, 4-pentenyl group, or the like; and the alkoxycarbonyl group includes ethoxycarbonyl group or the like.

Examples of the dimerized thiourea derivative of Formula [1] used in the present invention include, but are not limited to, the following:
4,4'-di(phenylthiocarbamoylamino)diphenylmethane, 4,4'di-(benzylthiocarbamoylamino)diphenylmethane, 4,4'di-(benzoylthiocarbamoylamino)diphenylmethane, 4,4'di-(ethylthiocarbamoylamino)diphenylmethane, 4,4'-di(n-butylthiocarbamoylamino)diphenylmethane, 4,4'-di(allylthiocarbamoylamino)diphenylmethane, 4,4'-di(ethoxycarbonylthiocarbamoylamino)diphenylmethane, 4,4'-di(phenylthiocarbamoylamino)diphenylether, 4,4'-di(p-tolylthiocarbamoylamino)diphenylether, 4,4'-di(tert-butylthiocarbamoylamino)diphenylether, 4,4'-di(benzylthiocarbamoylamino)diphenylether, 4,4'-di(benzoylthiocarbamoylamino)diphenylether, 4,4'-di(phenylthiocarbamoylamino)diphenylsulfone, 4,4'-di(p-chlorophenylthiocarbamoylamino)diphenylsulfone, 4,4'-di(iso-butylbenzylthiocarbamoylamino)diphenylsulfone, 4,4'-di(benzylthiocarbamoylamino)diphenylsulfone, 4,4'-di(benzoylthiocarbamoylamino)diphenylsulfone, 4,4'-di(phenylthiocarbamoylamino)diphenylsulfide, 4,4'-di(o-tolylthiocarbamoylamino)diphenylsulfide, 4,4'-di(dodecylthiocarbamoylamino)diphenylsulfide, 4,4'-di(benzylthiocarbamoylamino)diphenylsulfide, 4,4'-di(phenylthiocarbamoylamino)benzanilide, 4,4'-di(cyclohexylthiocarbamoylamino)benzanilide, 4,4'-di (benzylthiocarbamoylamino)benzanilide, 4,4'-di(phenylthiocarbamoylamino)diphenylethane, 4,4'-di(m-tolylthiocarbamoylamino)diphenylethane, 4,4'-di(octadecylthiocarbamoylamino)diphenylethane, 4,4'-di(benzylthiocarbamoylamino)diphenylethane, 4,4'-di(diphenylthiocarbamoylamino)-3,3'-dimethyldiphenylmethane, 4,4'-di(p-methoxyphenylthiocarbamoylamino)-3,3'-dimethyldiphenylmethane, 4,4'-di(benzylthiocarbamoylamino)-3,3'-dimethyldiphenylmethane, 4,4'-di(benzoylthiocarbamoylamino)-3,3'-dimethyldiphenylmethane, 4,4'-di(benzylthiocarbamoylamino)diphenylamine, 4,4'-di(benzylthiocarbamoylamino)diphenylamine, 4,4'-di(benzoylthiocarbamoylamino)diphenylamine, 4,4'-di(benzylthiocarbamoylamino)diphenylfluoropropane, and 4,4'-di(benzoylthiocarbamoylamino)diphenylhexafluoropropane.

Further, examples of the dimerized thiourea derivative of Formula [2] used in the present invention include, but are not limited to, the following:

1,3-di(benzylthiocarbamoylamino)benzene, 1,3-di(benzoylthiocarbamoylamino)-2-methylbenzene, 1,3-di(benzylthiocarbamoylamino)-5-chlorobenzene, 1,3-di(benzylthiocarbamoylamino)-4-methoxybenzene, 1,3-di(benzoylthiocarbamoylamino)-2,4,6-trimethylbenzene, 1,4-di(benzylthiocarbamoylamino)benzene, 1,4-di(benzoylthiocarbamoylamino)-2-chlorobenzene, 1,4-di(benzylthiocarbamoylamino)-2-methylbenzene, 1,4-di(benzoylthiocarbamoylamino)-2,5-dimethylbenzene, 1,4-di(benzylthiocarbamoylamino)-2,3,5,6-tetramethylbenzene, 1,4-di(benzoylthiocarbamoylamino)-2-chloro-5-methylbenzene, 4,4-di(benzylthiocarbamoylamino)-3,3'-dimethoxybenzidine, 4,4-di(benzoylthiocarbamoylamino)-3,3'-dimethoxybenzidine, 4,4-di(benzylthiocarbamoylamino)benzidine, 4,4-di(benzylthiocarbamoylamino)-3,3'-dimethylbenzidine, 4,4-di(benzylthiocarbamoylamino)-3,3'-dichlorobenzidine, 4,4-di(benzylthiocarbamoylamino)-3,3'6,6'-tetrachlorobenzidine, 4,4-di(benzoylthiocarbamoylamino)-3,3',6,6'-tetrachlorobenzidine, 1,5-di(benzylthiocarbamoylamino)naphthalene, and 1,5-di(benzoylthiocarbamoylamino)naphthalene.

The compounds of Formulae [1] and [2] of the present invention can be produced by using a reaction of monoisothiocyanate compounds and diamines.

Specifically, approximately 2 molar equivalents of a monoisothiocyanate are added to 1 mole of a diamine. Usable solvents are those which dissolve diamines and monoisothiocyanates, including aromatic hydrocarbons such as benzene, toluene, xylene, and the like; halogenated hydrocarbons such as chloroform, dichloromethane, chlorobenzene, and the like; ethers such as diethylether, tetrahydrofuran, and the like; nitriles such as acetonitrile, propionitrile, and the like; esters such as ethyl acetate and the like; ketones such as acetone, methylethylketone, and the like; non-proton donating polar solvents such as dimethylformamide, dimethylsulfoxide, and the like; alcohols such as methanol, ethanol, and the like; or mixtures thereof. The reaction temperature is 0° to 150° C., preferably 20° to 80° C.

Practical examples of the compounds of Formulae [1] and [2] are shown above, which are symmetrical compounds, however, the present invention is not limited to these symmetrical compounds, but asymmetrical compounds are also included.

The dimerized thiourea compound of Formula [1] has two thiourea structures, which can be considered as a compound in which the two thiourea structures are linked by two aromatic compounds. Of dimerized thiourea compounds of Formula [1], especially those of Formulae [3]–[4] are novel compounds.

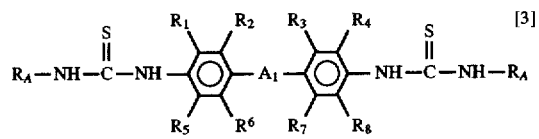

[3]

(wherein $A_1$ denotes $CH_2$, $(CH_2)_2$, S, O, $SO_2$, CONH, NH, or $C(CF_3)_2$. $R_A$ denotes a substituted or unsubstituted alkyl group having 1 to 18 carbon atoms, a substituted or unsubstituted aralkyl group having 7 to 30 carbon atoms, a substituted or unsubstituted acyl group having 2 to 20 carbon atoms, a substituted or unsubstituted alkenyl group having 2 to 20 carbon atoms, or a substituted or unsubstituted alkoxycarbonyl group having 2 to 20 carbon atoms. $R_1$, $R_2$, $R_3$, $R_4$, $R_5$, $R_6$, $R_7$, and $R_8$ denote the same as those in Formula [1].)

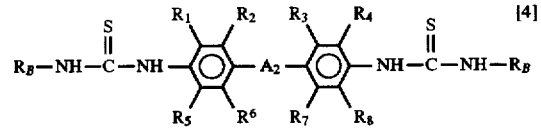

[4]

(wherein $A_2$ denotes S, O, $SO_2$, CONH, NH, or $C(CF_3)_2$. $R_B$ denotes a substituted or unsubstituted aryl group having 6 to 30 carbon atoms. $R_1$, $R_2$, $R_3$, $R_4$, $R_5$, $R_6$, $R_7$, and $R_8$ denote the same as those in Formula [1].)

Of the thiourea compounds of Formula [3], those of Formulae [5]–[6] are more preferable.

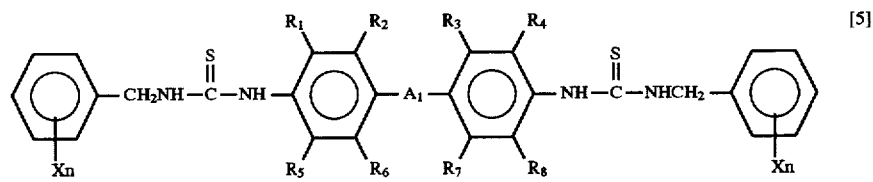

[5]

(wherein $A_1$ denotes $CH_2$, $(CH_2)_2$, S, O, $SO_2$, CONH, NH, or $C(CF_3)_2$. $R_1$, $R_2$, $R_3$, $R_4$, $R_5$, $R_6$, $R_7$, and $R_8$ denote the same as those in Formula [1]. X is a lower alkyl group having 1 to 6 carbon atoms, lower alkoxy group having 1 to 6 carbon atoms, halogen atom, or hydrogen atom. n is an integer from 1 to 3.)

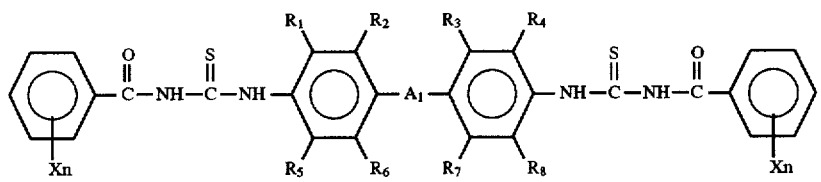

(wherein $A_1$ denotes $CH_2$, $(CH_2)_2$, S, O, $SO_2$, CONH, NH, or $C(CF_3)_2$. $R_1$, $R_2$, $R_3$, $R_4$, $R_5$, $R_6$, $R_7$, and $R_8$ denote the same as those in Formula [1]. X is a lower alkyl group having 1 to 6 carbon atoms, lower alkoxy group having 1 to 6 carbon atoms, halogen atom, or hydrogen atom. n is an integer from 1 to 3.)

The thiourea compounds of Formula [4] can be broadly classified into the following Formulae [7]–[11] by the group ($A_2$) linking two aromatic rings.

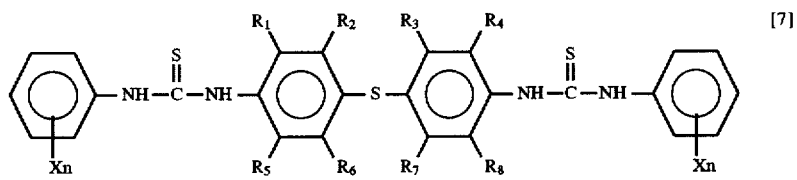

(wherein $R_1$, $R_2$, $R_3$, $R_4$, $R_5$, $R_6$, $R_7$, and $R_8$ denote the same as those in Formula [1]. X and n are the same as those in Formula [5].)

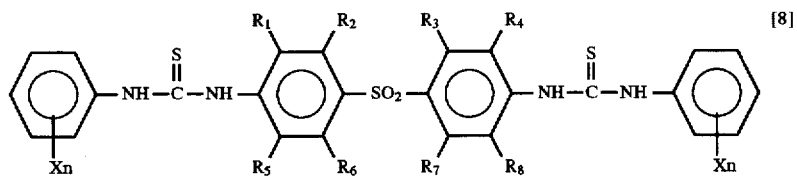

(wherein R1, R2, R3, R4, R5, R6, R7, and R8 denote the same as those in Formula [1]. X and n are the same as those in Formula [5].)

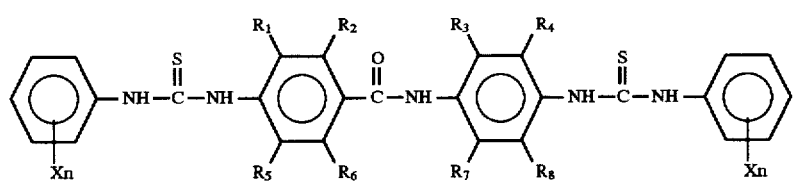

(wherein $R_1$, $R_2$, $R_3$, $R_4$, $R_5$, $R_6$, $R_7$, and $R_8$ denote the same as those in Formula [1]. X and n are the same as those in Formula [5].)

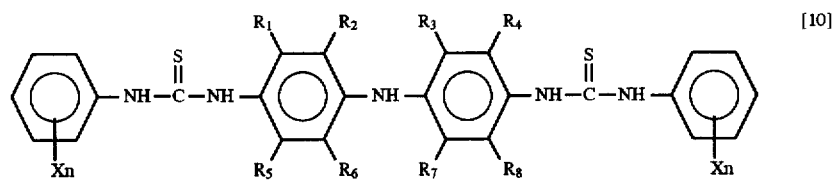

(wherein $R_1$, $R_2$, $R_3$, $R_4$, $R_5$, $R_6$, $R_7$, and $R_8$ denote the same as those in Formula [1]. X and n are the same as those in

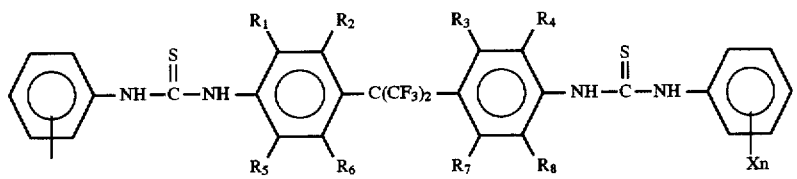
(wherein $R_1$, $R_2$, $R_3$, $R_4$, $R_5$, $R_6$, $R_7$, and $R_8$ denote the same as those in Formula [1]. X and n are the same as those in Formula [5].)
For example, compounds of Formulae [7] and [8] include the following.
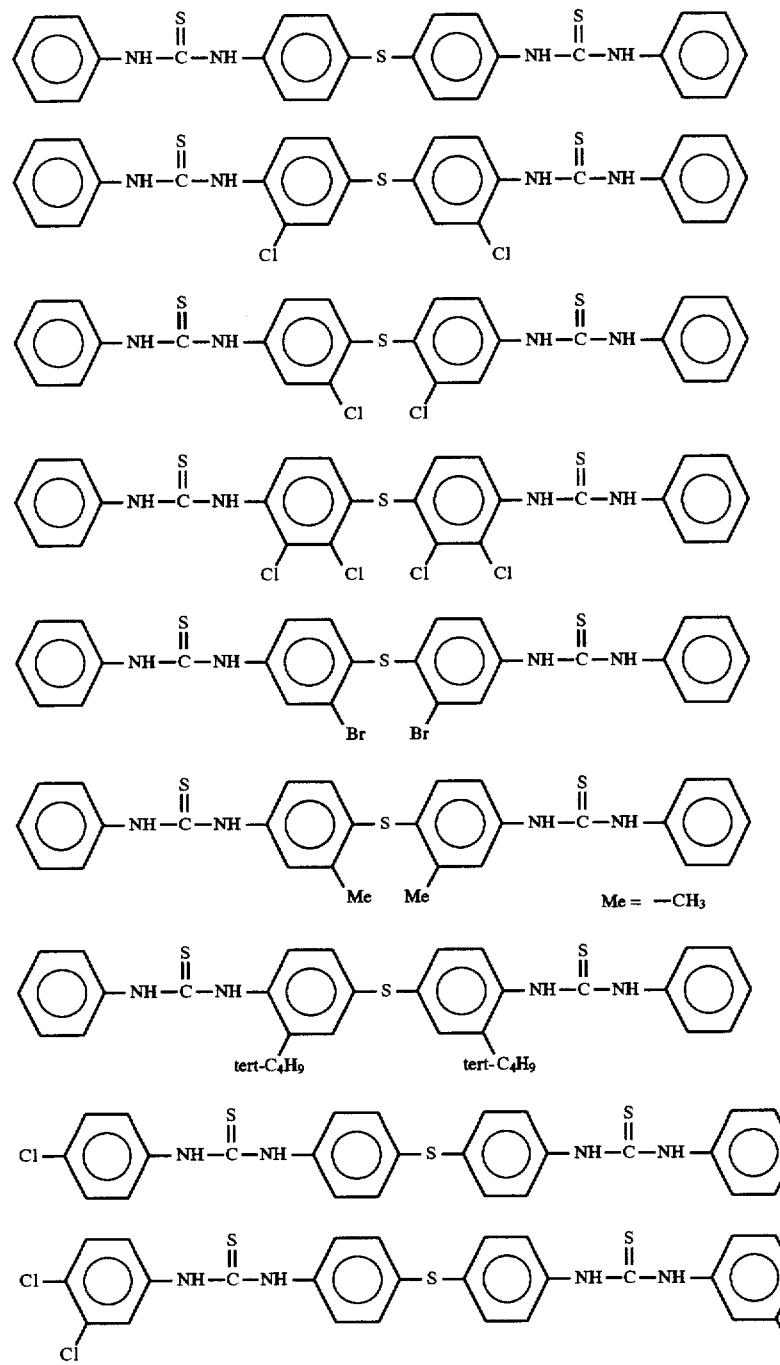

-continued
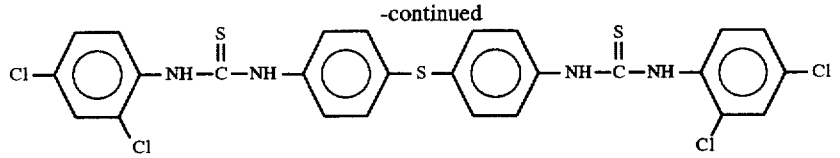
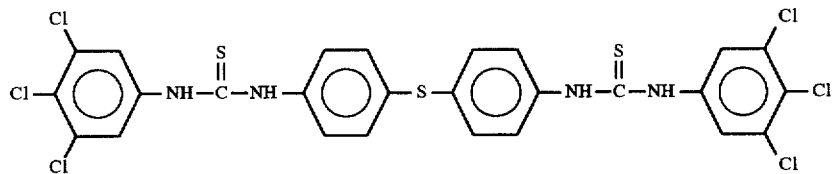
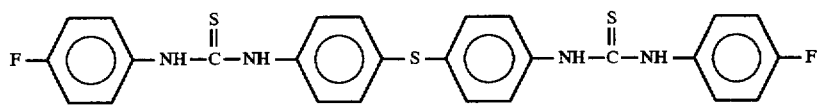
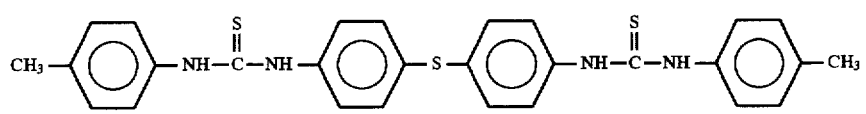
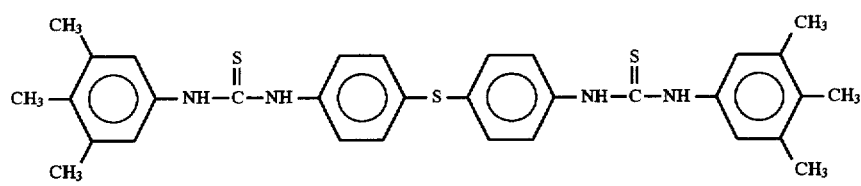
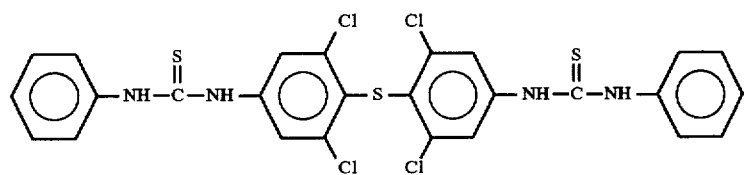
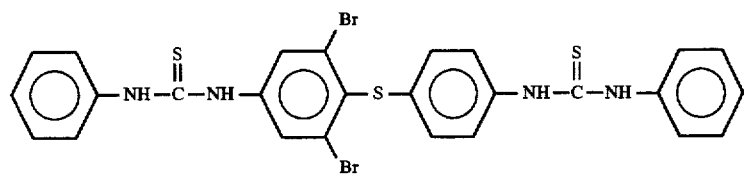
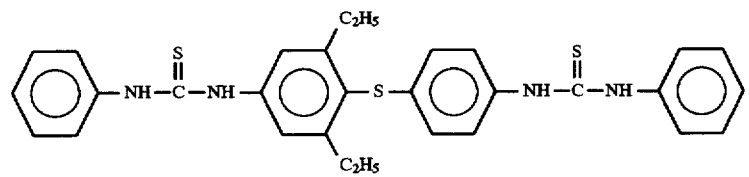
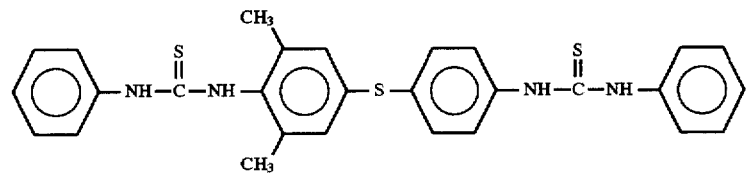
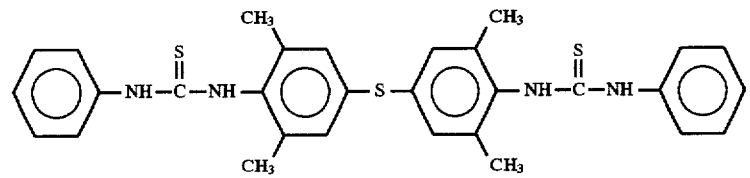

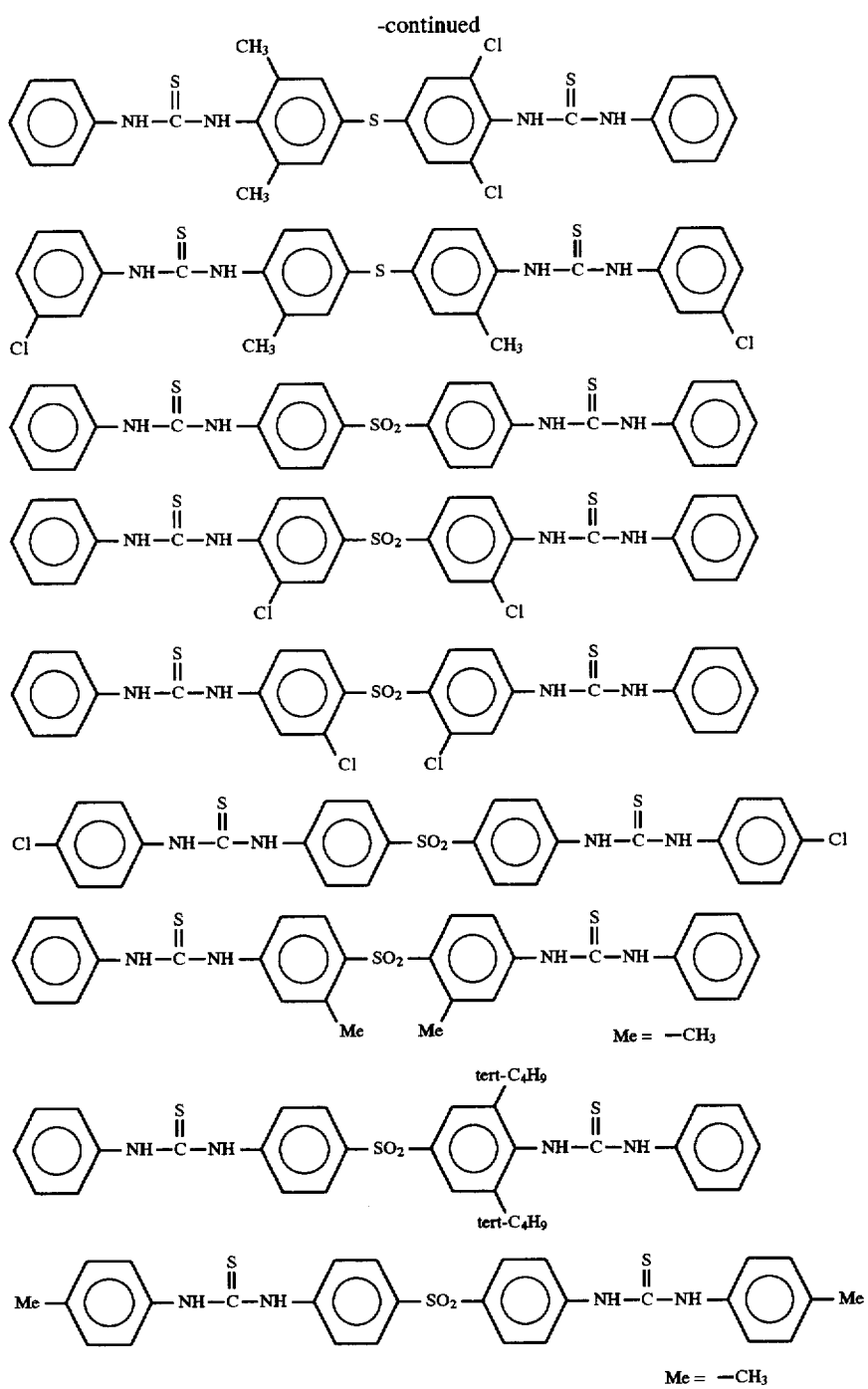

On the other hand, the dimerized thiourea compound of Formula [2] has two thiourea structures, which can be considered as a compound in which the thiourea structures are linked by a single aromatic compound. Of dimerized thiourea compounds of Formula [2], especially the dimerized thiourea compound of Formula [12] is a novel compound.

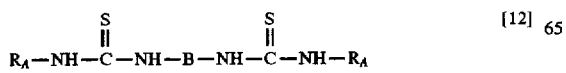

(wherein $R_A$ denotes the same as that in Formula [3], and B denotes a substituted or unsubstituted benzene ring, naphthalene ring, or biphenyl ring.)

Of the thiourea compounds of Formula [12], those of Formulae [13]–[14] are more preferable.

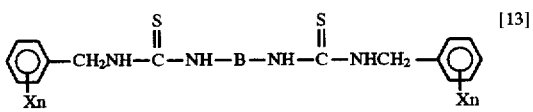

(wherein B denotes the same as that in Formula [2], and X and n denote the same as those in Formula [5].)

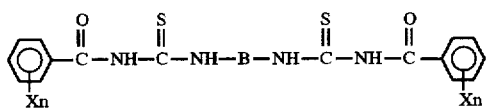

(wherein B denotes the same as that in Formula [2], and X and n denotes the same as those in Formula [5].)

The copper compound used in the present invention can preferably be at least one copper compound selected from the group consisting of copper compounds of an organic acid of Formula [15], copper bis-acetylacetonate, and copper hydroxide:

$$(Y-Z)_mCu \qquad [15]$$

(wherein Y denotes a substituted or unsubstituted alkyl group, a substituted or unsubstituted cycloalkyl group, a substituted or unsubstituted aryl group, a substituted or unsubstituted aralkyl group, or heterocyclic residue, Z is COO, SO$_4$, SO$_3$, PO$_4$, and m is an integer from 1 to 4.) Practical examples of the compounds of Formula [15] include, but are not limited to, the following:

Copper stearate, copper palmitate, copper oleate, copper behenate, copper laurate, copper caprate, copper caprylate, copper caproate, copper valerate, copper isobutyrate, copper 4-cyclohexylbutyrate, copper butyrate, copper propionate, copper acetate, copper formate, copper benzoate, copper toluate, copper t-butylbenzoate, copper chlorobenzoate, copper dichlorobenzoate, copper trichlorobenzoate, copper bromobenzoate, copper iodobenzoate, copper phenylbenzoate, copper benzoylbenzoate, copper nitrobenzoate, copper aminobenzoate, copper oxalate, copper malonate, copper succinate, copper glutarate, copper adipate, copper pimelate, copper suberate, copper azelaate, copper sebacate, copper citrate, copper phthalate, copper monoalkylester phthalate, copper monoacryloylester phthalate, copper naphthenate, copper naphthalenecarboxylate, copper diphenylamine-2-carboxylate, copper tartarate, copper gluconate, copper octylate, copper benzenesulfonate, copper p-toluenesulfonate, copper 2,5-dimethylbenzenesulfonate, copper 2-methoxycarbonyl-5-methylsulfonate, copper dodecylbenzenesulfonate, copper naphthalenesulfonate, copper aminonaphthalenesulfonate, copper dodecylsulfate, copper α-naphthylphosphate, copper stearyl-phosphate, copper laurylphosphate, copper di-2-ethylhexylphosphate, and copper isodecylphosphate.

Each of the above copper compound and the dimerized thiourea derivative alone has no absorption in the near-infrared region (780 nm–2,500 nm), or slightly absorbs a specific wavelength, and the absorption in the near-infrared region is not substantially changed even when each of the compounds alone is heat treated. Further, a composition comprising a mere mixture of the copper compound and the dimerized thiourea derivative does not provide a substantial change in near-infrared absorption. However, when the composition is heat treated, they immediately react to have a nearly uniform and strong absorption over the entire near-infrared region. Therefore, the composition comprising a mixture of the dimerized thiourea derivative and the copper compound is a superior near-infrared absorbent composition, and a reaction product obtained by heating the composition is a very good near-infrared absorbent.

Degree of the near-infrared absorption can be flexibly controlled by adjusting the types and ratio of the dimerized thiourea derivative and the copper compound, heating temperature, heating time, and the like. The ratio of the dimerized thiourea derivative and the copper compound is normally about 8:2 to 1:2 in molar ratio, preferably 2:1 to 1:1, the heating temperature is 100° to 250° C., preferably 120° to 180° C., and a heating time of several milliseconds is sufficient.

Various applications can be considered utilizing the properties. For example, when the near-infrared absorbent composition is provided with heat energy, since the portion provided with the heat energy is changed to near-infrared absorbent but has almost no absorption in the visible region, the composition can be incorporated in a heating pattern or a near-infrared detection apparatus, and an appropriate visualization means is used to obtain the recording image. By using a laser light having a wavelength in the near-infrared region as a heat source, a noncontacting visible image recording system can be obtained.

Further, utilizing the property of having a strong absorption over nearly the entire near-infrared region, a near-infrared absorbent molding and a heat wave shielding material can be obtained.

The near-infrared absorbent molding can be obtained by melting the dimerized thiourea compound and the copper compound or a composition comprising a mixture thereof with a resin and then molding, or by heat molding a near-infrared absorbent obtained by previously heating the raw materials to above a predetermined temperature with a resin, in the form of granules, films, sheets, boards, or desired three-dimensional shapes. Further, the near-infrared absorbent or the near-infrared absorbent composition can be sprayed, coated, or impregnated to a desired substrate, dried, and heated to endow the substrate with a near-infrared absorbing property. Since near-infrared light acts as a heat source, when a highly transparent resin is used as the resin or the substrate, the material can also be used as a heat wave shielding material which blocks the near-infrared region.

The dimerized thiourea compound and the copper compound can be added in amounts of 0.05 to 5% by weight, preferably 0.1 to 1% by weight, based on the resin to obtain a near-infrared absorbent resin composition which is less colored, good in visible light transmittance, and superior in near-infrared absorbing property.

The resin can be known thermoplastic resins such as polyethylene, polyvinylchloride, poly(meth)acrylic acid or poly(meth)acrylic esters, polycarbonate, polystyrene, and styrene-butadiene copolymers; known thermosetting resins such as urea resins, melamine resins, and epoxy resins; and natural resins such as rosin and dammar. Thermoplastic resins are widely used for producing moldings. For example, for glazing applications, polycarbonate, polymethyl methacrylate, and the like are used to good advantage in terms of transparency and strength.

In the production of moldings, since the molding temperature depends on the type of resin used, a dimerized thiourea derivative of type that does not decompose at the temperature can be selected to prevent unpleasant gas evolution.

In molding, it is preferable that the resin is mixed with the near-infrared absorbent composition of the present invention by a tumbler, mixer, blender, or the like to obtain a master batch and, as needed, additives such as a dye for coloring, a pigment, an antioxidant, a stabilizer such as an ultraviolet absorbent, a fire-retardant agent, a plasticizer, and the like to obtain a compounding material.

Further, the near-infrared absorbent resin and its molding can also be obtained by mixing a polymerizable raw material with the dimerized thiourea compound of the present invention and the copper compound, and heat polymerized in the presence of a radical polymerization initiator. The dimerized thiourea derivative and the copper compound are used in total amounts of about 0.1 to 0.5 parts by weight, preferably 0.2 to 1.0 part by weight, based on 100 parts by weight of the polymerizable raw material to obtain a sufficient effect.

The polymerizable raw material is at least one of known radical polymerizable unsaturated monomers such as (meth)acrylic acid, (meth)acrylic esters, styrene, olefins, vinylchloride, and the like, and a prepolymer of these polymerizable monomers dissolved in the polymerizable monomer can also be used as the polymerizable raw material. The polymerizable raw material can be polymerized by known polymerization means to obtain polymers such as poly(meth)acrylic acid, poly(meth)acrylic esters, polyolefins, polyvinylchloride, polyvinylidenechloride, polystyrene, polyesters, polyvinylacetate, polyvinylalcohol, and the like.

Radical polymerization is initiated by the action of heat, light, or radiation, and normally carried out in the presence of an initiator or photosensitizer. Further, by the polymerization condition, the process is classified into block polymerization, solution polymerization, emulsion polymerization, and suspension polymerization.

Typical examples of the radical polymerization initiator are azo compound type initiators and peroxide type initiators. Practical examples of the azo compound type initiator include 2,2'-azo-bis-isobutyronitrile, 2,2'-azo-bis-2,4-dimethylvaleronitrile, 1,1'-azo-bis-1-cyclohexanecarbonitrile, methyl 2,2'-azo-bis-isobutyrate, and the like; and practical examples of the peroxide type initiator include benzoylperoxide, di-1-butylperoxide, diisopropylperoxydicarbonate, dicyclohexylperoxydicarbonate, and the like. In the present invention, when polymerization is carried out using a peroxide type initiator, the near-infrared absorption may be reduced depending on the type and amount of the initiator. Therefore, the use of an azo compound type initiator is preferable.

For poly(meth)acrylic acid, poly(meth)acrylic ester, polystyrene, and polyvinylacetate, a molding can be produced simultaneously with block polymerization of each monomer. Further, when two or more types of monomers are combined and block polymerized, a copolymer can be obtained.

Further, for polyolefin, polyvinylchloride, polyvinylidenechloride, polycarbonate, polyester, and polyvinylacetate, films can be produced by polymerization of each monomer followed by melt extrusion. For polyvinylchloride, polycarbonate, methacrylic resins, polystyrene, polypropylene, and polyethylene, plates and films can be produced by a solution flow method after polymerization.

In photopolymerization, a photopolymerization initiator and, as needed, a visible light sensitizer are added to the above polymerizable raw material, and polymerization is carried out. Practical examples of the photopolymerization initiator include acetophenone, 2,2'-diethoxyacetophenone, benzophenone, 4,4'-bisdimethylaminobenzophenone, benzoin, benzoinethylether, and the like, of which one or more types are used.

Polymerization is carried out by a method in which a mixture mainly comprising the above polymerizable raw material, the near-infrared absorbent composition or the near-infrared absorbent of the present invention, and a photopolymerization initiator is coated on a substrate, or sealed in a transparent made of glass, plastics, or the like, and then irradiated with light.

Further, an object already formed to a certain shape can also be endowed with a near-infrared absorbent property by spraying, coating, or printing a slurry comprising a composition of the dimerized thiourea derivative of the present invention and the copper compound dissolved or dispersed with a binder on a substrate, followed by drying and heating, or by spraying, coating, or printing a slurry comprising the near-infrared absorbent of the present invention and a binder. Further, the substrate can also be endowed with a near-infrared absorbent property by a method in which a solution of the resin composition containing the near-infrared absorbent composition in a solvent or a molten liquid thereof is coated on the substrate, dried, and heat treated.

For example, when the dimerized thiourea derivative and the copper compound are dissolved in a silicone-based hard coating agent, coated on the substrate, and heat treated, polysiloxane condenses to form a glass-like substance, and the dimerized thiourea derivative and the copper compound react to yield a near-infrared absorbent, thereby obtaining a near-infrared absorbent glass-like protective coating. The silicone-based hard coating agent mainly comprises three-functional and four-functional organoalkoxysilane monomers, which are hydrolyzed in the presence of a solvent and an acid or base, and partially condensed to obtain a polysiloxane, which is dissolved in a solvent such as alcohol, cellosolve, ketone, or the like, mixed with a curing catalyst and, according to a required function, mixed with various additives to obtain a sol. The sol can be cured at a low temperature of about 120° to 150° C. by selecting a catalyst, thereby coating a resin having a low heat distortion temperature such as polymethylmethacrylate with a near-infrared absorbent glass-like protective film without deformation of the resin.

The total amount of the dimerized thiourea compound and the copper compound is 5 to 50 parts by weight based on 100 parts by weight of solid of the silicone-based hard coating agent, and the molar ratio of the dimerized thiourea derivative and the copper compound is 8:2 to 1:2.

Since a plastic sheet or film comprising the near-infrared absorbent contained in a highly transparent plastic has a wide and strong absorption in the near-infrared region, it can be used as a heat wave shielding material.

The heat wave shielding plastic sheet is required to have the following quality: (1) it cuts off sunlight energy as much as possible, and allows visible light to pass, (2) physical strength is not reduced, (3) the heat wave shielding effect does not vary with time, and (4) it is clear and least turbid as possible.

Heat wave shielding performance of the heat wave shielding material can be evaluated for sunlight transmittance and visible light transmittance according to JIS R 3106.

The visible light transmittance represents a visual transmittance to daylight (standard light D 65), of which the greater value is the lighter. The sunlight transmittance represents a transmittance to sunlight, that is, radiations of the near-ultraviolet, visible, and near-infrared regions which comes from the sun passing through the atmosphere to the ground, of which the lower the value, the higher is the cutting rate.

The sunlight energy distributes in 0.3 to 2.5 μm in wavelength. Of the total sunlight energy, that of the visible light region (0.38 to 0.78 μm) accounts for about 45%, and the remaining 50% is in the near-infrared region (0.78 to 2.5 μm).

When there is no sunlight blocking material, the sunlight transmittance and visible light transmittance are 100. For a shielding material which passes all of near-infrared rays and cuts off all of visible light (the visible light transmittance is 0), from the wavelength ratio of sunlight, the sunlight transmittance is 55, but it is dark to human eyes. Such a heat wave shielding material is not directed to by the present invention. Further, as the visible light transmittance is increased, the sunlight transmittance of course increases, and the result becomes worse. On the contrary, in an ideal condition where all of visible light is passed (visible light transmittance 100) and all of near-infrared rays are cut off, the sunlight transmittance is 50. Then, since the objective heat wave shielding material is required to pass visible light as much as possible and cut off near-infrared rays as much as possible, in the present invention a heat wave shielding efficiency is defined by Formula [A]:

$$\eta = [(E-Y)/50] \times 100 \quad [A]$$

(wherein E is a visible light transmittance, Y is a sunlight transmittance, and 50 indicates a sunlight transmittance of an ideal heat wave shielding material.)

That is, in an ideal condition as a heat wave shielding material, $$\eta_o = [(100-50)/50] \times 100 = 100 \ (\%),$$

and when all of light is passed, $$\eta = [(100-100)/50] \times 100 = 0 \ (\%).$$

Therefore, the greater the $\eta$ value, the better the heat wave shielding efficiency of the plate.

When the heat wave shielding material of the present invention which can sufficiently transmit visible light while cutting off near-infrared light is used, sunlight passed through the material feels no heat. The material can be used in summer in exterior applications for roofing, exterior materials, and the like such as in a carport, sunroom, terrace, and the like to supply bright and cool light, thereby suppressing temperature increase in rooms and reducing operation of air conditioners.

Further, the heat wave shielding material of the present invention blocks near-infrared light by absorbing it. Finally the absorbed near-infrared light is partly converted to heat, and emits radiation energy according to the temperature of the substance. The radiation energy is 3.0 to 30 µm in wavelength. Therefore, when the heat wave shielding material is used in the interiors, a greenhouse effect occurs unless an efficient heat dissipation is effected but, when it is used in winter, operation of heaters can be reduced.

Since the heat wave shielding material is required to pass visible light as much as possible, the material resin desirably has a high transparency and, at the same time, it is necessary to select a dimerized thiourea compound and a copper compound which dissolve in the polymerizable raw material. For the copper compound, copper salt of phthalic acid derivative which is readily soluble in the polymerizable raw material as disclosed in Japanese Patent Laid-open Publication 3-246256 can be used.

The transparent polymer is preferably based on an unsaturated monomer such as (meth)acrylic acid, (meth)acrylic ester, styrene, vinylacetate, or the like as the polymerizable monomer and, particularly, one which is based mainly on (meth)acrylic ester is preferable. The (meth)acrylic ester is a (meth)acrylic ester of a compound having monohydric or polyhydric hyroxyl groups or in which a prepolymer of the (meth)acrylic ester is dissolved.

The polymerization condition is not specifically limited but, for example, when the dimerized thiourea compound and the copper compound and a polymerization initiator are dissolved in methylmethacrylate and block polymerized in a mold, an initial-stage polymerization (pre-polymerization) is carried out at 40° to 90° C. for 2 to 3 hours, and a post-stage polymerization (main polymerization) is carried out at 90° to 140° C. for 2 to 3 hours to obtain a near-infrared absorbent resin plate.

It is also a preferable method that a resin material containing the dimerized thiourea compound and the copper compound is mixed with a photopolymerization initiator, and photopolymerized to obtain a near-infrared absorbent plate.

The thus obtained heat wave shielding material, for example, a 1 mm thick near-infrared absorbent methacrylic sheet obtained by a method in which 100 parts by weight of methacrylic resin is mixed with 0.3 parts by weight of the near-infrared absorbent composition and extrusion injection molded has a sunlight transmittance of 55 to 60% and a visible light transmittance of 70 to 75%. Further, a 2 mm thick near-infrared absorbent methacrylic sheet containing 0.5 parts by weight of the near-infrared absorbent composition has a sunlight transmittance of 15 to 25% and a visible light transmittance of 30 to 40%. At either concentration, the heat wave shielding efficiency is 35 to 45%.

Further, the heat wave shielding material can also cut off ultraviolet rays. Since such an ultraviolet shielding material is transparent, that is, passes visible light, it is effectively used in sunglasses, window glass, and the like which can block harmful ultraviolet rays without inconvenience in viewing objects such as in seashore, skiing ground, high mountains, welding place, and the like.

BRIEF DESCRIPTION OF THE DRAWINGS

FIG. 1-B: A transmission spectrum of a 3 mm thick PMMA plate.

FIG. 2-D: A transmission spectrum of a 2 mm thick PS plate.

FIG. 3-D: A transmission spectrum of a 2 mm thick PS plate.

FIG. 4-G: A transmission spectrum of a 1 mm thick PMMA plate.

FIG. 5-I: A transmission spectrum of a 2 mm thick PMMA plate.

FIG. 5-J: A transmission spectrum of a brown-colored 2 mm thick PMMA plate.

DESCRIPTION OF PREFERRED EMBODIMENTS

Figure 1:
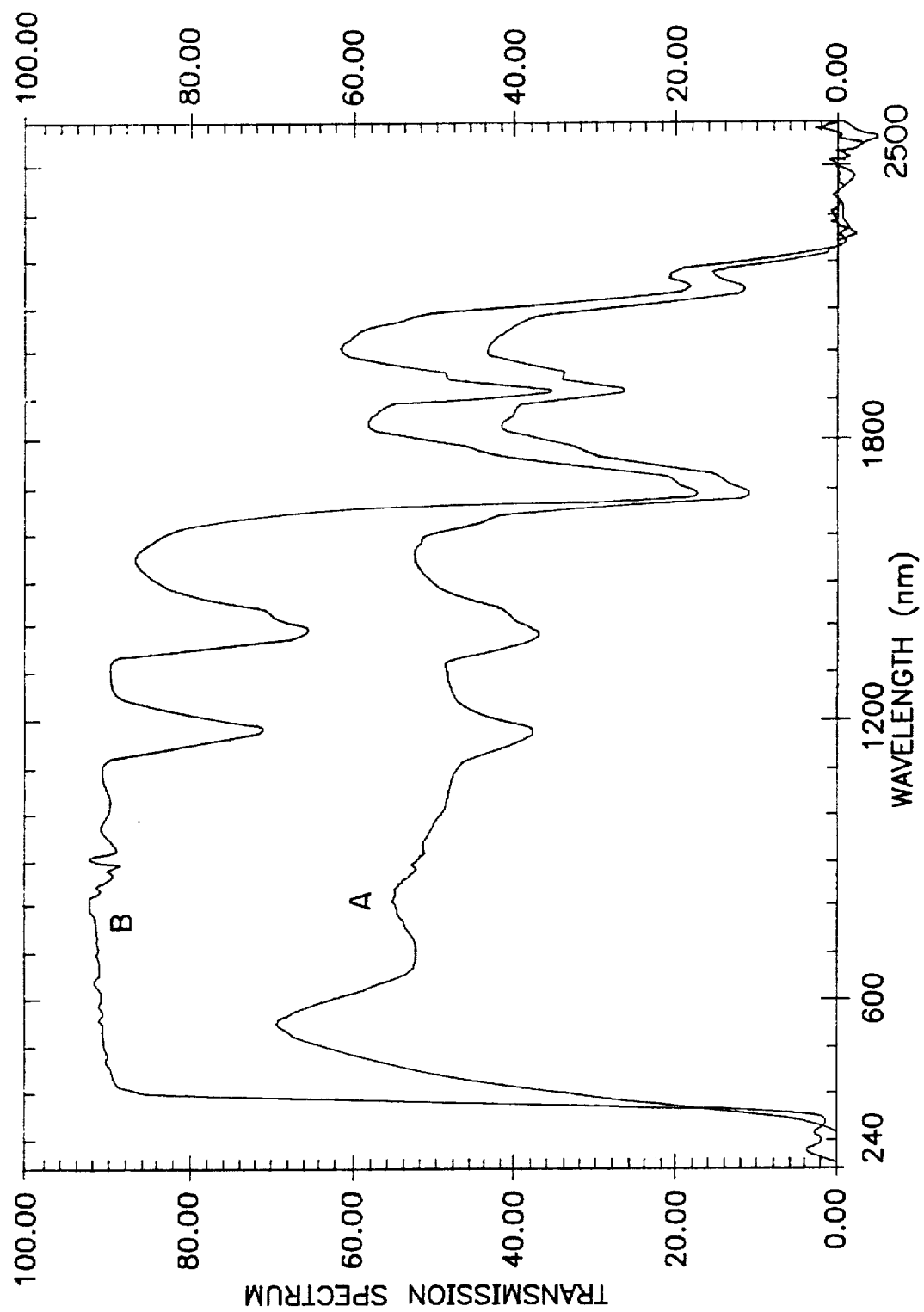
FIG. 1-A: A transmission spectrum of a 3.05 mm thick PMMA plate obtained in Example 37.

The present invention will be described further in detail with reference to the embodiments.

EXAMPLE 1

(Synthesis of Compound A-1)

4,4'-di(phenylthiocarbamoylamino)diphenylmethane 4,4'-Diaminodiphenylmethane (0.991 g, 5 mM) was dissolved in 20 ml of ethyl acetate, and 2 equivalents of phenylisothiocyanate (1.352 g, 10 mM) was added. The mixture was stirred at 80° C. for 10 minutes. After cooling, the reaction mixture was filtered, and washed with ethylacetate/n-hexane to obtain 1.79 g (75.9% yield) of a a colorless crystal of compound A-1.

Melting point: 181° C.

$^1$H-NMR (DMSO-$d_6$) ppm $\delta$=3.97 (2H, s, $\phi$-$CH_2$-$\phi$) $\delta$=7.17–7.55 (18H, m, —$C_6H_4$— x 2, $C_6H_5$— x 2) $\delta$=9.02 (4H, broad s, —NH— x 2)

EXAMPLE 2

(Synthesis of Compound A-2)

4,4'-di(benzylthiocarbamoylamino)diphenylmethane 4,4'-Diaminodiphenylmethane (0.991 g, 5 mM) was dissolved in 20 ml of ethyl acetate, and 2 equivalents of benzylisothiocyanate (1.492 g, 10 mM) was added. The mixture was stirred at 80° C. for 10 minutes. After cooling, the reaction mixture was filtered, and washed with ethylacetate/n-hexane to obtain 2.24 g (90.2% yield) of a colorless crystal of compond A-2.

Melting point: 200° C. (dec.)

$^1$H-NMR (DMSO-$d_6$) ppm $\delta$=3.87 (2H, s, $\phi$-$CH_2$-$\phi$) $\delta$=4.72 (4H, d, J=5.5, $\phi$-$CH_2$-$\phi$) $\delta$=7.18–7.36 (18H, m, —$C_6H_4$— x 2, $C_6H_5$— x 2) $\delta$=8.11 (2H, broad s, —$CH_2$NH— x 2) $\delta$=9.55 (2H, broad s, —NH— x 2)

EXAMPLE 3

(Synthesis of Compound A-3)

4,4'-di(benzoylthiocarbamoylamino)diphenylmethane 4,4'-Diaminodiphenylmethane (0.496 g, 2.5 mM) was dissolved in 20 ml of ethyl acetate, and 2 equivalents of benzoylisothiocyanate (0.816 g, 5 mM) was added. The mixture was stirred at 25° C. for 10 minutes. After cooling, the reaction mixture was filtered, and washed with ethylacetate/n-hexane to obtain 1.26 g (96.1% yield) of a colorless crystal of compound A-3.

Melting point: 221° C.

$^1$H-NMR (DMSO-$d_6$) ppm $\delta$=3.98 (2H, s, $\phi$-$CH_2$-$\phi$) $\delta$=7.30–7.99 (18H, m, —$C_6H_4$— x 2, $C_6H_5$— x 2) $\delta$=11.56 (2H, broad s, —NH— x 2) $\delta$=12.58 (2H, broad s, —NH— x 2)

EXAMPLE 4

(Synthesis of Compound A-4)

4,4'-di(ethylthiocarbamoylamino)diphenylmethane 4,4'-Diaminodiphenylmethane (0.991 g, 5 mM) was dissolved in 15 ml of ethyl acetate, and 2 equivalents of ethylisothiocyanate (0.872 g, 10 mM) was added. The mixture was stirred at 80° C. for 30 minutes. After cooling, the reaction mixture was filtered, and washed with ethylacetate/n-hexane to obtain 1.21 g (64.9% yield) of a colorless crystal of compound A-4.

Melting point: 161° C.

$^1$H-NMR (DMSO-$d_6$) ppm $\delta$=1.09 (3H, t, J=14.3, —$CH_3$ x 2) $\delta$=3.46 (2H, t, J=12.6, —$CH_2$x 2) $\delta$=3.86 (2H, s, $\phi$-$CH_2$-$\phi$) $\delta$=7.22 (8H, dd, J=8.4, 8.3, —$C_6H_4$— x 2) $\delta$=7.67 (2H, broad s, —$CH_2$NH— x 2) $\delta$=9.36 (2H, broad s, —NH— x 2)

EXAMPLE 5

(Synthesis of Compound A-5)

4,4'-di(n-butylthiocarbamoylamino)diphenylmethane 4,4'-Diaminodiphenylmethane (0.991 g, 5 mM) was dissolved in 15 ml of ethyl acetate, and 2 equivalents of n-butylisothiocyanate (1.152 g, 10 mM) was added. The mixture was stirred at 80° C. for 30 minutes. After cooling, the reaction mixture was filtered, and washed with ethylacetate/n-hexane to obtain 1.47 g (68.5% yield) of a colorless crystal of compound A-5.

Melting point: 174° C.

$^1$H-NMR (DMSO-$d_6$) ppm $\delta$=0.89 (3H, t, J=14.6, —$CH_3$ x 2) $\delta$=1.29 (4H, dd, J=7.1, 7.6, —$CH_2$— x 2) $\delta$=1.50 (4H, t, J=14.4, —$CH_2$ x 2) $\delta$=3.46 (4H, broad dd, J=5.5, —$CH_2$ x 2) $\delta$=3.86 (2H, s, $\phi$-$CH_2$-$\phi$) $\delta$=7.23 (8H, dd, J=7.6, 7.4, —$C_6H_4$— x 2) $\delta$=7.67 (2H, broad s, —$CH_2$NH x 2) $\delta$=9.36 (2H, broad s, —NH— x 2)

EXAMPLE 6

(Synthesis of Compound A-6)

4,4'-di(allylthiocarbamoylamino)diphenylmethane 4,4'-Diaminodiphenylmethane (0.991 g, 5 mM) was dissolved in 15 ml of ethyl acetate, and 2 equivalents of allylisothiocyanate (0.991 g, 10 mM) was added. The mixture was stirred at 80° C. for 60 minutes. After cooling, the reaction mixture was filtered, and washed with ethylacetate/n-hexane to obtain 1.01 g (51.1% yield) of a colorless crystal of compound A-6.

Melting point: 155° C.

$^1$H-NMR (DMSO-$d_6$) ppm $\delta$=3.87 (2H, s, $\phi$-$CH_2$-$\phi$) $\delta$=4.12 (4H, collapsed t, $CH_2$=CH—$CH_2$ x 2) $\delta$=5.07–5.19 (4H, m, $CH_2$=CH—$CH_2$ x 2) $\delta$=5.83–5.92 (2H, m, $CH_2$=CH—$CH_2$ x 2) $\delta$=7.23 (8H, dd, J=8.3, 8.3, —$C_6H_4$— x 2) $\delta$=7.77 (2H, broad s, —$CH_2$NH x 2) $\delta$=9.47 (2H, broad s, —NH— x 2)

EXAMPLE 7

(Synthesis of Compound A-7)

4,4'-di($\beta$-phenylethylthiocarbamoylamino)diphenylmethane 4,4'-Diaminodiphenylmethane (0.496 g, 2.5 mM) was dissolved in 15 ml of ethyl acetate, and 2 equivalents of ethylisothiocyanate (0.816 g, 5 mM) was added. The mixture was stirred at 80° C. for 30 minutes. After cooling, the reaction mixture was filtered, and washed with ethylacetate/n-hexane to obtain 0.50 g (38.0% yield) of a colorless crystal of compound A-7.

Melting point: 145° C.

$^1$H-NMR (DMSO-$d_6$) ppm $\delta$=2.85 (3H, t, J=14.3, —$CH_3$ x 2) $\delta$=3.69 (2H, t, J=12.6, —$CH_2$ x 2) $\delta$=3.87 (2H, s, $\phi$-$CH_2$-$\phi$) $\delta$=7.08–7.33 (18H, m, —$C_6H_4$—x 2, $C_6H_5$— x 2) $\delta$=7.66 (2H, broad s, —$CH_2$NH— x 2) $\delta$=9.49 (2H, broad s, —NH— x 2)

EXAMPLE 8

(Synthesis of Compound A-8)

4,4'-di(ethoxycarbonylthiocarbamoylamino)diphenylmethane 4,4'-Diaminodiphenylmethane (0.496 g, 2.5 mM) was dissolved in 20 ml of ethyl acetate, and 10 ml of an ethyl acetate solution of 2 equivalents of ethoxycarbonylisothiocyanate (0.816 g, 5 mM) was added. The mixture was stirred at 80° C. for 10 minutes. After cooling, the reaction mixture was filtered, and washed with ethyl acetate/n-hexane to obtain 1.07 g (92.8% yield) of a colorless crystal of compound A-8.

Melting point: 172° C.

$^1$H-NMR (DMSO-d$_6$) ppm δ=1.25 (3H, t, J=14.1, —CH$_3$ x 2) δ=3.94 (2H, s, φ-CH$_2$-φ) δ=4.20 (2H, t J=12.6, O—CH$_2$ x 2) δ=7.26, 7.51 (8H, dd, J=8.4, 8.3, —C$_6$H$_4$— x 2) δ=11.24 (2H, broad s, —NH— x 2) δ=11.48 (2H, broad s, —NH— x 2)

EXAMPLE 9 (Synthesis of Compound A-9)

4,4'-di(phenylthiocarbamoylamino)diphenylether 4,4'-Diaminodiphenylether (1.001 g, 5 mM) was dissolved in 30 ml of acetone, and 2 equivalents of phenylisothiocyanate (1.352 g, 10 mM) was added. The mixture was stirred at 40° C. for 75 minutes. After cooling, the reaction mixture was filtered, and washed with acetone/n-hexane to obtain 1.96 g (83.4% yield) of a colorless crystal of compound A-9.

Melting point: 201° C.

$^1$H-NMR (DMSO-d$_6$) ppm δ=6.97–7.48 (18H, m, —C$_6$H$_4$x 2, C$_6$H$_5$— x 2) δ=9.76 (2H, broad s, —NH— x 2)

EXAMPLE 10 (Synthesis of Compound A-10)

4,4'-di(benzylthiocarbamoylamino)diphenylether 4,4'-Diaminodiphenylether (1.001 g, 5 mM) was dissolved in 30 ml of acetone, and 2 equivalents of benzylisothiocyanate (1.492 g, 10 mM) was added. The mixture was stirred at 55° C. for 15 minutes. After cooling, the reaction mixture was filtered, and washed with acetone/n-hexane to obtain 1.19 g (47.8% yield) of a colorless crystal of compound A-10.

Melting point: 194° C. (dec.)

$^1$H-NMR (DMSO-d$_6$) ppm δ=4.75 (4H, d, J=5.4, φ-CH$_2$— x 2) δ=6.97–7.42 (18H, m, —C$_6$H$_4$— x 2, C$_6$H$_5$— x 2) δ=8.08 (2H, broad s, —CH$_2$NH— x 2) δ=9.54 (2H, broad s, —NH— x 2)

EXAMPLE 11

(Synthesis of Compound A-11)

4,4'-di(benzoylthiocarbamoylamino)diphenylether 4,4'-Diaminodiphenylether (0.501 g, 2.5 mM) was dissolved in 30 ml of acetone, and 2 equivalents of benzoylisothiocyanate (0.816 g, 5 mM) was added. The mixture was stirred at 55° C. for 15 minutes. After cooling, the reaction mixture was filtered, and washed with acetone/n-hexane to obtain 1.23 g (93.2% yield) of a colorless crystal of compound A-11.

Melting point: 213° C.

$^1$H-NMR (DMSO-d$_6$) ppm δ=7.09–8.01 (18H, m, —C$_6$H$_4$— x 2, C$_6$H$_5$— x 2) δ=11.59 (2H, broad s, —NH— x 2) δ=12.56 (2H, broad s, —NH— x 2)

EXAMPLE 12

(Synthesis of Compound A-12)

4,4'-di(benzylthiocarbamoylamino)diphenylsulfone 4,4'-Diaminodipheylsulfone (1.242 g, 5 mM) was dissolvedi n 10 ml of a mixture of acetone and ethyl acetate, and 2 equivalents of benzylisothiocyanate (1.492 g, 10 mM) was added. The mixture was stirred at 55° C. for 90 minutes. After cooling, the reaction mixture was filtered, and washed with acetone/n-hexane to obtain 1.75 g (64.1% yield) of a colorless crystal of compound A-12.

Melting point: 203° C. (dec.)

1H-NMR (DMSO-d$_6$) ppm δ=4.74 (4H, d, J=5.2, φ-CH$_2$— x 2) δ=7.24–7.88 (18H, m, —C$_6$H$_4$— x 2, C$_6$H$_5$— x 2) δ=8.50 (2H, broad s, —CH$_2$NH— x 2) δ=9.97 (2H, broad s, —NH— x 2)

EXAMPLE 13

(Synthesis of Compound A-13)

4,4'-di(benzoylthiocarbamoylamino)diphenylsulfone 4,4'-Diaminodiphenylsulfone (0.621 g, 2.5 mM) was dissolved in 10 ml of a mixture of acetone and ethyl acetate, and 2 equivalents of benzoylisothiocyanate (0.816 g, 5 mM) was added. The mixture was stirred at 55° C. for 90 minutes. After cooling, the reaction mixture was filtered, and washed with acetone/n-hexane to obtain 1.30 g (90.5% yield) of a colorless crystal of compound A-13.

Melting point: 219° C. (dec.)

$^1$H-NMR (DMSO-d$_6$) ppm δ=7.52–8.03 (18H, m, —C$_6$H$_4$— x 2, C$_6$H$_5$— x 2) δ=11.76 (2H, broad s, —NH— x 2) δ=12.74 (2H, broad s, —NH— x 2)

EXAMPLE 14

(Synthesis of Compound A-14)

4,4'-di(benzylthiocarbamoylamino)diphenylsulfide 4,4'-Diaminodiphenylsulfide (1.082 g, 5 mM) was dissolved in 10 ml of ethyl acetate, and 2 equivalents of benzylisothiocyanate (1.492 g, 10 mM) was added. The mixture was stirred at 55° C. for 90 minutes. After cooling, the reaction mixture was filtered, and washed with acetone/n-hexane to obtain 1.00 g (77.7% yield) of a colorless crystal of compound A-14.

Melting point: 183° C. (dec.)

$^1$H-NMR (DMSO-d$_6$) ppm δ=4.73 (4H, d, J=5.2, φ-CH$_2$— x 2) δ=7.23–7.49 (18H, m, —C$_6$H$_4$— x 2, C$_6$H$_5$— x 2) δ=8.27 (2H, broad s, —CH$_2$NH— x 2) δ=9.71 (2H, broad s, —NH— x 2)

EXAMPLE 15

(Synthesis of Compound A-15)

4,4'-di(phenylthiocarbamoylamino)benzanilide 4,4'-Diaminobenzanilide (0.658 g, 2.5 mM) was dissolved in 20 ml of acetone, and 2 equivalents of phenylisothiocyanate (0.676 g, 5 mM) was added. The mixture was stirred at 55° C. for 10 minutes. After cooling, the reaction mixture was filtered, and washed with acetone/n-hexane to obtain 0.90 g (72.3% yield) of a colorless crystal of compound A-15.

Melting point: 206° C. (dec.)

$^1$H-NMR (DMSO-d$_6$) ppm δ=7.12–7.95 (18H, m, —C$_6$H$_4$— x 2, C$_6$H$_5$— x 2) δ=9.75 (2H, broad s, —NH— x 2) δ=10.04 (2H, broad s, —NH— x 2) δ=10.19 (1H, broad s, —NH—)

EXAMPLE 16

(Synthesis of Compound A-16)

4,4'-di(benzylthiocarbamoylamino)benzanilide 4,4'-Diaminobenzanilide (0.568 g, 2.5 mM) was dissolved in 20 ml of acetone, and 2 equivalents of benzylisothiocyanate (0.746 g, 5 mM) was added. The mixture was stirred at 55° C. for 10 minutes. After cooling, the reaction mixture was filtered, and washed with acetone/n-hexane to obtain 0.57 g (43.4% yield) of a colorless crystal of compound A-16.

Melting point: 207° C.

$^1$HNMR (DMSO-$d_6$) ppm $\delta$=4.75 (4H, t, J=12.8, $\phi$-CH$_2$— x 2) $\delta$=7.23–7.93 (18H, m, —C$_6$H$_4$— x 2, C$_6$H$_5$— x 2) $\delta$=8.08 (1H, broad s, —CH$_2$NH—) $\delta$=8.43 (1H, broad s, —CH$_2$NH—) $\delta$=9.56 (1H, broad s, —NH—) $\delta$=9.91 (1H, broad s, —NH—) $\delta$=10.17 (1H, s, —NH—)

EXAMPLE 17

(Synthesis of Compound A-17)

4,4'-di(phenylthiocarbamoylamino)diphenylethane 4,4'-Diaminodiphenylethane (0.531 g, 2.5 mM) was dissolved in 20 ml of ethyl acetate, and 2 equivalents of phenylisothiocyanate (0.676 g, 5 mM) was added. The mixture was stirred at 40° C. for 60 minutes. After cooling, the reaction mixture was filtered, and washed with ethyl acetate/n-hexane to obtain 0.91 g (75.4% yield) of a colorless crystal of compound A-17.

Melting point: 198° C. (dec.)

$^1$H-NMR (DMSO-$d_6$) ppm $\delta$=2.86 (4H, s, $\phi$-CH$_2$—CH$_2$-$\phi$) $\delta$=7.09–7.49 (18H, m, —C$_6$H$_4$— x 2, C$_6$H$_5$— x 2) $\delta$=9.74 (4H, broad s, —NH— x 2)

EXAMPLE 18

(Synthesis of Compound A-18)

4,4'-di(benzylthiocarbamoylamino)diphenylethane 4,4'-Diaminodiphenylethane (0.531 g, 2.5 mM) was dissolved in 20 ml of ethyl acetate, and 2 equivalents of benzylisothiocyanate (0.746 g, 5 mM) was added. The mixture was stirred at 80° C. for 60 minutes. After cooling, the reaction mixture was filtered, and washed with ethylacetate/n-hexane to obtain 1.11 g (86.9% yield) of a colorless crystal of compound A-18.

Melting point: 197° C.

$^1$-NMR (DMSO-$d_6$) ppm $\delta$=2.84 (4H, s, $\phi$-CH$_2$—CH$_2$-$\phi$) $\delta$=4.73 (4H, d, J=5.2, $\phi$-CH$_2$— x 2) $\delta$=7.19–7.34 (18H, m, —C$_6$H$_4$— x 2, C$_6$H$_5$— x 2) $\delta$=8.10 (2H, broad s, —CH$_2$NH— x 2) $\delta$=9.55 (2H, broad s, —NH— x 2)

EXAMPLE 19

(Synthesis of Compound A-19)

4,4'-di(benzylthiocarbamoylamino)-3,3'-dimethyldiphenylmethane 4,4'-Diamino-3,3'-dimethyldiphenylmethane (0.566 g, 2.5 mM) was dissolved in 10 ml of ethyl acetate, and 2 equivalents of benzylisothiocyanate (0.746 g, 5 mM) was added. The mixture was stirred at 80° C. for 10 minutes. After cooling, the reaction mixture was filtered, and washed with ethyl acetate/n-hexane to obtain 1.00 g (77.7% yield) of a pale pink crystal of compound A-19.

Melting point: 187° C.

$^1$H-NMR (DMSO-$d_6$) ppm $\delta$=2.12 (6H, s, $\phi$-CH$_3$ x 2) $\delta$=3.83 (2H, s, $\phi$-CH$_2$-$\phi$) $\delta$=4.68 (4H, d, J=5.0, $\phi$-CH$_2$— x 2) $\delta$=7.06–7.34 (16H, m, —C$_6$H$_3$— x 2, C$_6$H$_5$— x 2) $\delta$=7.84 (2H, broad s, —CH$_2$NH— x 2) $\delta$=9.12 (2H, broad s, —NH— x 2)

EXAMPLE 20

(Synthesis of Compound A-20)

4,4'-di(benzoylthiocarbamoylamino)-3,3'-dimethyldiphenylmethane 4,4'-Diamino-3,3'-dimethyldiphenylmethane (0.566 g, 2.5 mM) was dissolved in 10 ml of ethyl acetate, and 2 equivalents of benzoylisothiocyanate (0.816 g, 5 mM) was added. The mixture was stirred at 80° C. for 10 minutes. After cooling, the reaction mixture was filtered, and washed with ethyl acetate/n-hexane to obtain 1.24 g (89.7% yield) of a pale pink crystal of compound A-20.

Melting point: 220° C. (dec.)

$^1$H-NMR (DMSO-$d_6$) ppm $\delta$=2.24 (6H, s, $\phi$-CH$_3$ x 2) $\delta$=3.92 (2H, s, $\phi$-CH$_2$—$\phi$) $\delta$=7.14–8.01 (16H, m, —C$_6$H$_3$— x 2, C$_6$H$_5$— x 2) $\delta$=11.60 (2H, broad s, —NH— x 2) $\delta$=12.23 (2H, broad s, —NH— x 2)

EXAMPLE 21

(Synthesis of Compound A-21)

4,4'-di(benzylthiocarbamoylamino)diphenylamine 4,4'-Diaminodiphenylamine sulfate (1.486 g, 5 mM) was dissolved in 100 ml of water, sodium hydroxide (0.40 g, 10 mM) was added and stirred, and extracted with 150 ml of ethyl acetate. The resulting ethyl acetate solution was thoroughly washed with water, dewatered, and vacuum concentrated to about 20 ml. Precipitated insoluble substances were filtered out, and 2 equivalents of benzylisothiocyanate (1.492 g, 10 mM) were added to the filtrate. The mixture was stirred at 80° C. for 30 minutes, after cooling, the reaction mixture was filtered, and washed with ethyl acetate/n-hexane to obtain 0.97 g (39.0% yield) of a pale pink crystal of compound A-21.

Melting point: 179° C.

$^1$H-NMR (DMSO-$d_6$) ppm $\delta$=4.72 (4H, d, J=5.6, $\phi$-CH$_2$— x 2) $\delta$=7.01–7.33 (18H, m, —C$_6$H$_4$— x 2, C$_6$H$_5$— x 2) $\delta$=7.93 (2H, broad s, —CH$_2$NH— x 2) $\delta$=8.20 (1H, broad s, —NH—) $\delta$=9.42 (2H, s, —NH— x 2)

EXAMPLE 22

(Synthesis of Compound A-22)

4,4'-di(benzoylthiocarbamoylamino)diphenylamine 4,4'-Diaminodiphenylamine sulfate (1.486 g, 5 mM) was dissolved in 100 ml of water, sodium hydroxide (0.40 g, 10 mM) was added and stirred, and extracted with 150 ml of ethyl acetate. The resulting ethyl acetate solution was thoroughly washed with water, dewatered, and vacuum concentrated to about 20 ml. Precipitated insoluble substances were filtered out, and an ethyl acetate solution of 2 equivalents of benzoylisothiocyanate (1.492 g, 10 mM) was added to the filtrate. The mixture was stirred at room temperature for 30 minutes, the reaction mixture was filtered, and washed with ethyl acetate/n-hexane to obtain 1.60 g (51.1% yield) of a light brown crystal of compound A-22.

Melting point: 210° C.

$^1$H-NMR (DMSO-$d_6$) ppm $\delta$=7.12–8.00 (18H, m, —C$_6$H$_4$— x 2, C$_6$H$_5$— x 2) $\delta$=8.47 (1H, s, —NH—) $\delta$=11.50 (2H, s, —NH— x 2) $\delta$=12.53 (2H, s, —NH— x 2)

EXAMPLE 23

(Synthesis of Compound A-23)

4,4'-di(benzoylthiocarbamoylamino)-diphenylhexafluoropropane 4,4'-Diaminodiphenylhexafluoropropane (0.363 g, 1 mM) was dissolved in 20 ml of ethyl acetate, and 2 equivalents of benzoylisothiocyanate (0.326 g, 2 mM) were added. The mixture was stirred at 80° C. for 60 minutes. After cooling, the reaction mixture was filtered, and washed with ethylacetate/n-hexane to obtain 0.671 g (97.3% yield) of a colorless crystal of compound A-23.

Melting point: 206° C. (dec.)

$^1$H-NMR (DMSO-d$_6$) ppm δ=7.41–8.01 (16H, m, —C$_6$H$_3$— x 2, C$_6$H$_5$— x 2) δ=11.67 (2H, broad s, —NH— x 2) δ=12.73 (2H, broad s, —NH— x 2)

EXAMPLE 24

(Synthesis of Compound A-24)

1,3-di(benzylthiocarbamoylamino)benzene m-Phenylenediamine (0.541 g, 5 mM) was dissolved in 20 ml of ethyl acetate, and 2 equivalents of benzylisothiocyanate (1.492 g, 10 mM) were added. The mixture was stirred at 80° C. for 10 minutes. After cooling, the reaction mixture was filtered, and washed with ethyl acetate/n-hexane to obtain 1.90 g (93.5% yield) of a white crystal of 1,3-dibenzylthiocarbamoylaminobenzene.

Melting point: 152° C.

1HNMR (Acetone-d$_6$) ppm δ=4.87 (4H, d, J=5.6, φ-CH$_2$ x 2) δ=7.16–7.40 (14H, m, —C$_6$H$_4$— x 2, C$_6$H$_5$— x 2) δ=7.73 (2H, broad t, —CH$_2$NH— x 2) δ=9.04 (4H, broad s, —NH— x 2)

EXAMPLE 25

(Synthesis of Compound A-25)

1,4-di(benzylthiocarbamoylamino)benzene p-Phenylenediamine (2.707 g, 25 mM) was dissolved in 20 ml of ethyl acetate, and 2 equivalents of benzylisothiocyanate (7.461 g, 50 mM) were added. The mixture was stirred at 80° C. for 30 minutes. After cooling, the reaction mixture was filtered, and washed with ethylacetate/n-hexane to obtain 6.26 g (61.6% yield) of a colorless crystal of compound A-25.

Melting point: 198° C.

$^1$H-NMR (DMSO-d$_6$) ppm δ=4.73 (4H, d, J=5.2, φ-CH2 x 2) δ=7.25–7.38 (14H, m, —C$_6$H$_4$— x 2, C$_6$H$_5$— x 2) δ=8.11 (2H, broad s, —CH$_2$NH— x 2) δ=9.59 (2H, broad s, —NH— x 2)

EXAMPLE 26

(Synthesis of Compound A-26)

1,4-di(benzoylthiocarbamoylamino)-2,5-dimethylbenzene 2,5-Dimethyl-p-phenylenediamine (0.340 g, 2.5 mM) was dissolved in 30 ml of ethyl acetate, and 2 equivalents of benzoylisothiocyanate (0.816 g, 5 mM) were added. The mixture was stirred at room temperature for 10 minutes. After cooling, the reaction mixture was filtered, and washed with ethyl acetate/n-hexane to obtain 1.14 g (98.6% yield) of a colorless crystal of compound A-26.

Melting point: 228° C. (dec.)

$^1$H-NMR (DMSO-d$_6$) ppm δ=2.26 (6H, s, φ-CH$_3$ x 2) δ=7.53–7.70 (12H, m, —C$_6$H$_2$—, C$_6$H$_5$— x 2) δ=11.69 (2H, broad s, —NH— x 2) δ=12.28 (2H, broad s, —NH— x 2)

EXAMPLE 27

(Synthesis of Compound A-27)

4,4'-di(benzoylthiocarbamoylamino)-3,3'-dimethoxybenzidine o-Anisidine (0.611 g, 2.5 mM) was dissolved in 30 ml of ethyl acetate, and 2 equivalents of benzoylisothiocyanate (0.816 g, 5 mM) were added. The mixture was stirred at room temperature for 10 minutes. After cooling, the reaction mixture was filtered, and washed with ethyl acetate/n-hexane to obtain 1.18 g (82.7% yield) of a colorless crystal of compound A-27.

Melting point: 250° C. (dec.)

$^1$H-NMR (DMSO-d$_6$) ppm δ=4.02 (6H, s, φ-CH$_3$— x 2) δ=7.37–8.73 (16H, m, —C$_6$H$_3$— x 2, C$_6$H$_5$— x 2) δ=11.51 (2H, broad s, —NH— x 2) δ=13.11 (2H, broad s, —NH— x 2)

EXAMPLE 28

(Synthesis of Compound A-28)

4,4'-di(benzoylthiocarbamoylamino)-3,3'-dichlorobenzidine o-Dichlorobenzidine (0.633 g, 2.5 mM) was dissolved in 30 ml of ethyl acetate, and 2 equivalents of benzoylisothiocyanate (0.816 g, 5 mM) were added. The mixture was stirred at room temperature for 10 minutes. After cooling, the reaction mixture was filtered, and washed with ethyl acetate/n-hexane to obtain 1.44 g (99.6% yield) of a pale yellow crystal of compound A-28.

Melting point: 225° C. (dec.)

$^1$H-NMR (DMSO-d$_6$) ppm δ=7.54–8.30 (16H, m, —C$_6$H$_3$— x 2, C$_6$H$_5$— x 2) δ=11.91 (2H, broad s, —NH— x 2) δ=12.83 (2H, broad s, —NH— x 2)

EXAMPLE 29

(Synthesis of Compound A-29)

1,5-di(benzylthiocarbamoylamino)naphthalene 1,5-Naphthalenediamine (0.791 g, 5 mM) was dissolved in 20 ml of ethyl acetate, and 2 equivalents of benzylisothiocyanate (1.492 g, 10 mM) were added. The mixture was stirred at 80° C. for 30 minutes. After cooling, the reaction mixture was filtered, and washed with ethylacetate/n-hexane to obtain 0.70 g (30.7% yield) of a colorless crystal of compound A-29.

Melting point: 176° C.

$^1$H-NMR (DMSO-d$_6$) ppm δ=4.70 (4H, d, J=5.8, φ-CH$_2$ x 2) δ=7.03–7.56 (16H, m, —C$_{10}$H$_6$— x 2, C$_6$H$_5$— x 2) δ=7.82 (2H, broad s, —CH$_2$NH— x 2) δ=9.57 (2H, s, —NH— x 2)

EXAMPLE 30

(Synthesis of Compound A-30)

4,4'-di(phenylthiocarbamoylamino)diphenylsulfide 4,4'-Diaminodiphenylsulfide (1.082 g, 5 mM) was dissolved in 10 ml of ethyl acetate, and 2 equivalents of phenylisothiocyanate (1.351 g, 10 mM) were added. The mixture was stirred at 55° C. for 90 minutes. After cooling, the reaction mixture was filtered, and washed with ethylacetate/n-hexane to obtain 1.10 g (45.2% yield) of a colorless crystal of compound A-30.

Melting point: 167° C.

$^1$H-NMR (DMSO-d$_6$) ppm δ=7.13 (2H, t, J=8.0) δ=7.29 (4H, t, J=8.0) δ=7.33 (4H, t, J=8.0) δ=7.47 (4H, t, J=8.0) δ=7.52 (4H, t, J=8.0) δ=9.89 (4H, broad s, —NH— x 4)

EXAMPLE 31

(Synthesis of Compound A-31)

4,4'-di(chlorophenylthiocarbamoylamino)diphenylsulfide 4,4'-Diaminodiphenylsulfide (1.082 g, 5 mM) were dissolved in 10 ml of ethyl acetate, and 2 equivalents of p-chlorophenylisothiocyanate (1.696 g, 10 mM) were added. The mixture was stirred at 55° C. for 90 minutes. After cooling, the reaction mixture was filtered, and washed with ethyl acetate/n-hexane to obtain 1.39 g (50.2% yield) of a colorless crystal of compound A-31.

Melting point: 193° C.

$^1$H-NMR (DMSO-$d_6$) ppm δ=7.30 (4H, d, J=8. 0) δ=7.38 (4H, d, J=8. 0) δ=7.50 (4H, d, J=8. 0) δ=9.95 (4H, broad s, —NH— x 4)

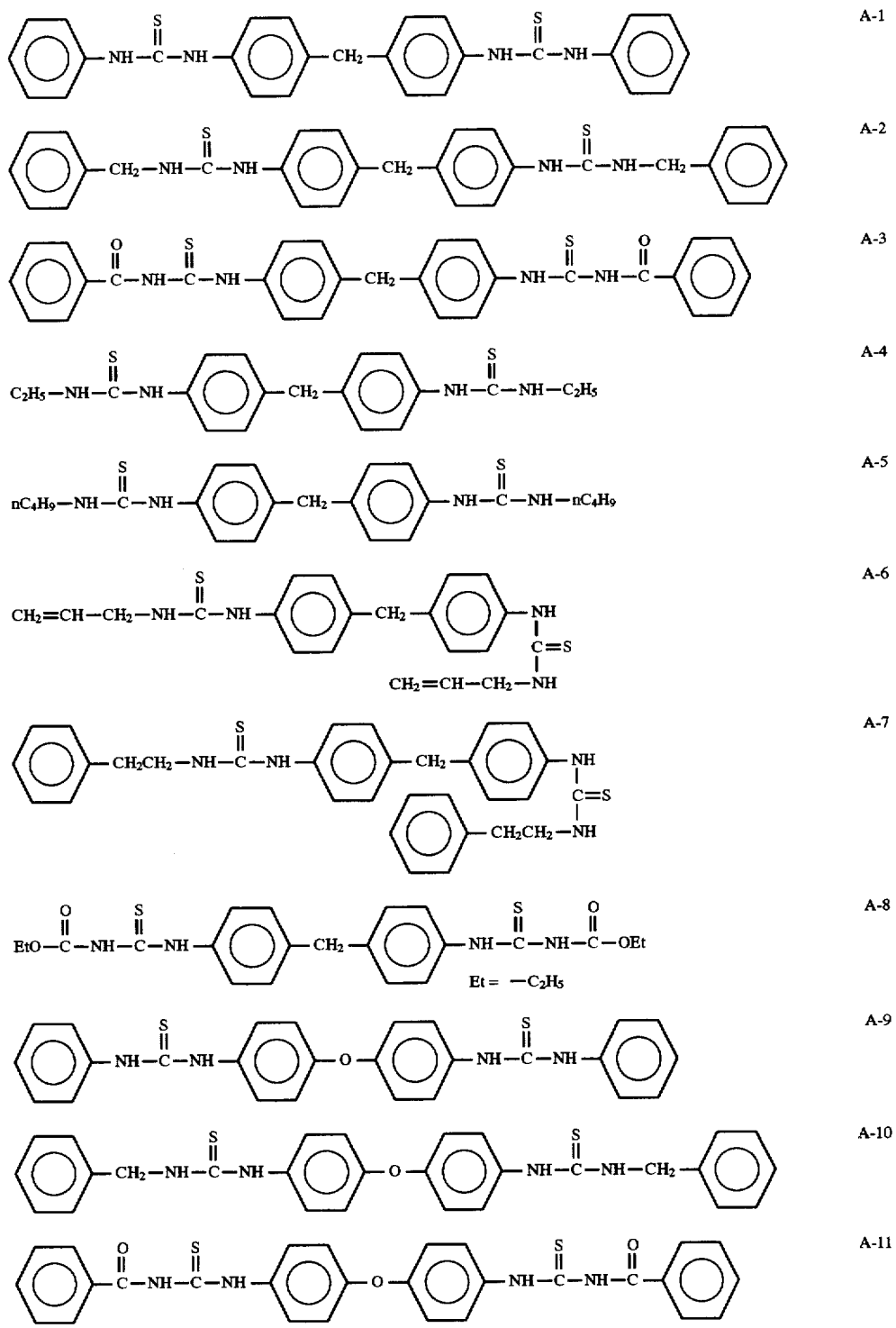

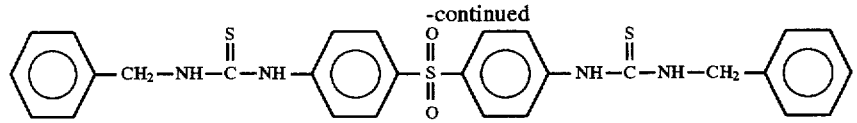 A-12
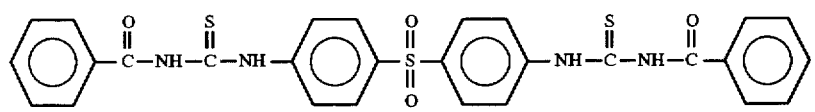 A-13
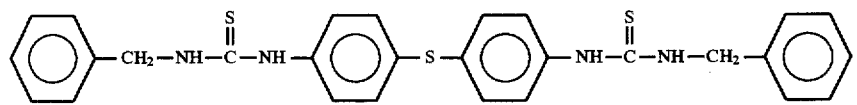 A-14
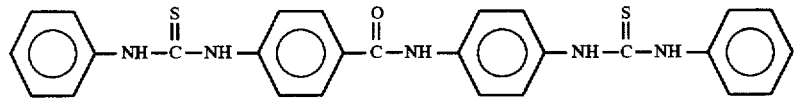 A-15
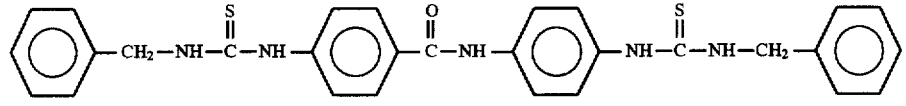 A-16
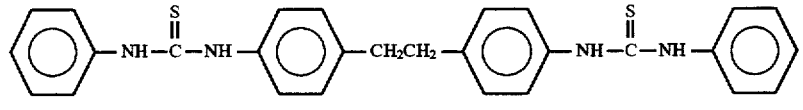 A-17
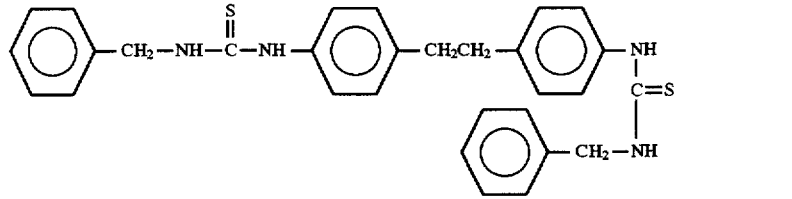 A-18
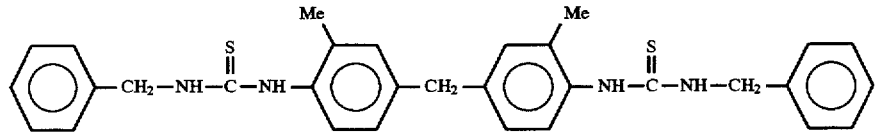 A-19
Me = —CH₃
 A-20
Me = —CH₃
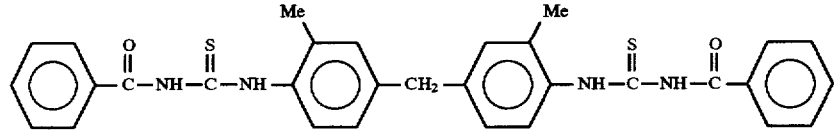 A-21
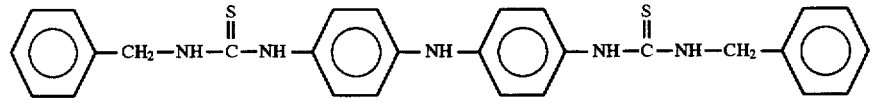 A-22
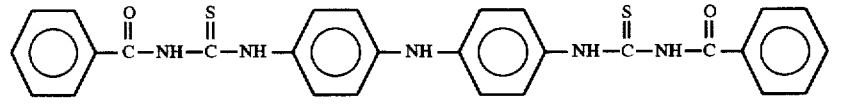

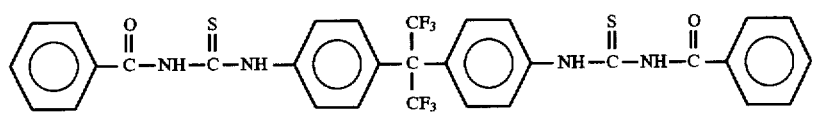
A-23

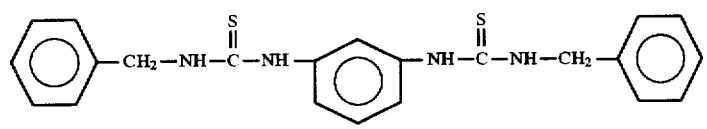
A-24

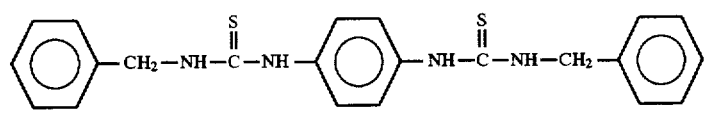
A-25

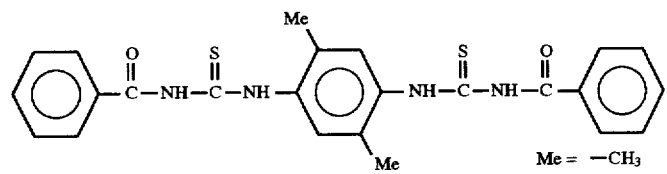
A-26

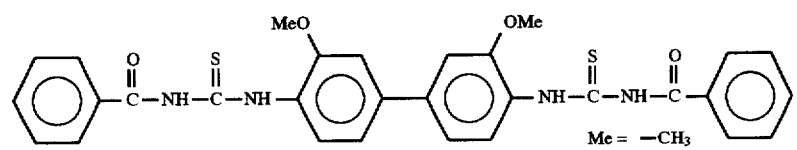
A-27

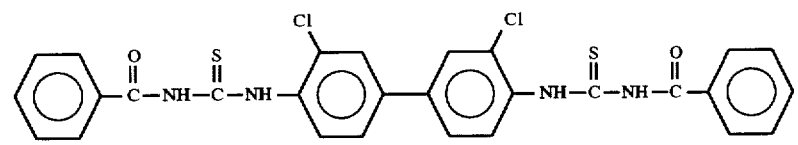
A-28

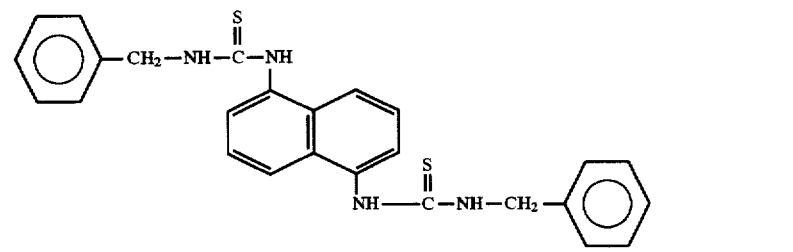
A-29

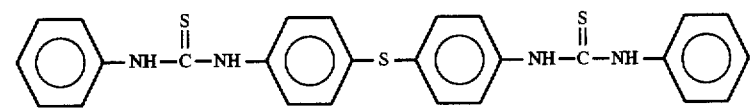
A-30

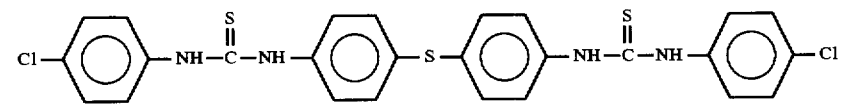
A-31

EXAMPLE 32

Thermal analysis of the dimerized thiourea derivatives in Examples 1 to 29 was carried out in air flow to determine decomposition temperatures of the compounds from thermal changes in weight from room temperature to 400° C. Comparing with decomposition temperatures of conventional thiourea compounds of Comparative Examples 1 to 3, the results are shown in Table 1.

TABLE 1

Decomposition temperatures of dimerized thiourea derivatives

| | Decomposition temperature (°C.) | | Decomposition temperature (°C.) |
|---|---|---|---|
| Example 1 | 183.4 | Example 16 | 211.1 |
| 2 | 210.5 | 17 | 198.0 |
| 3 | 223.7 | 18 | 204.7 |
| 4 | 200.3 | 19 | 220.1 |
| 5 | 184.8 | 20 | 219.9 |

TABLE 1-continued

Decomposition temperatures of dimerized thiourea derivatives

| | | | |
|---|---|---|---|
| 6 | 183.7 | 21 | 233.6 |
| 7 | 210.1 | 22 | 213.3 |
| 8 | 189.0 | 23 | 206.3 |
| 9 | 201.6 | 24 | 203.8 |
| 10 | 206.5 | 25 | 199.2 |
| 11 | 218.5 | 26 | 227.7 |
| 12 | 203.1 | 27 | 250.0 |
| 13 | 219.3 | 28 | 225.0 |
| 14 | 183.5 | 29 | 211.8 |
| 15 | 206.2 | | |

| Comparative | 1 | 1,3-Diphenylthiourea | 153.2 |
|---|---|---|---|
| Example | 2 | 1,3-Di-o-chlorophenylthiourea | 150.5 |
| | 3 | 1,3-Di-o-tolylthiourea | 152.0 |

The individual thiourea compounds shown in Comparative Examples decomposed at 150° to 155° C., whereas the decomposition temperatures of the compounds shown in Examples 1 to 29 were above 180° C. A dimerized thiourea compound, which is the most heat-resistant, decomposed at 250° C.

EXAMPLE 33

A composition comprising compound A-2 and copper stearate, mixed in a molar ratio of 2:1, was dry blended in an amount of 0.25 parts by weight with 100 parts by weight of polystyrene (PS, Nippon Steel Chemical ESTYRENE), and kneaded by an extruder at an extrusion temperature of 190° C. to produce a near-infrared absorbent PS pellet. During the kneading, types and amounts of evolving gases were determined using a g gas detection tube.

EXAMPLE 34

A composition comprising compound A-10 and copper stearate, mixed in a molar ratio of 3:1, was dry blended in an amount of 0.5 parts by weight with 100 parts by weight of polystyrene (PS, Nippon Steel Chemical ESTYRENE), and kneaded by an extruder at an extrusion temperature of 190° C. to produce a near-infrared absorbent PS pellet. During the kneading, types and amounts of evolving gases were determined using a gas detection tube.

EXAMPLE 35

A composition comprising compound A-12 and copper stearate, mixed in a molar ratio of 3:1, was dry blended in an amount of 0.4 parts by weight with 100 parts by weight of polymethylmethacrylate (PMMA, Sumitomo Chemical SUMIPEX), and kneaded by an extruder at an extrusion temperature of 200° C. to produce a near-infrared absorbent PMMA pellet. During the kneading, types and amounts of evolving gases were determined using a gas detection tube.

EXAMPLE 36

A composition comprising compound A-24 and copper β-acryloyloxypropylhydrogenphthalate, mixed in a molar ratio of 4:1, was dry blended in an amount of 0.3 parts by weight with 100 parts by weight of polymethylmethacrylate (PMMA, Sumitomo Chemical SUMIPEX), and kneaded by an extruder at an extrusion temperature of 200° C. to produce a near-infrared absorbent PMMA pellet. During the kneading, types and amounts of evolving gases were determined using a gas detection tube.

COMPARATIVE EXAMPLE 1

A composition comprising 1,3-diphenylthiourea and copper stearate, mixed in a molar ratio of 5:1, was dry blended in an amount of 0.5 parts by weight with 100 parts by weight of polystyrene (PS, Nippon Steel Chemical ESTYRENE), and kneaded by an extruder at an extrusion temperature of 190° C. to produce a near-infrared absorbent PS pellet. During the kneading, types and amounts of evolving gases were determined using a gas detection tube.

COMPARATIVE EXAMPLE 2

A composition comprising 1,3-di-tolylthiourea and copper monobutylphthalate, mixed in a molar ratio of 3:1, was dry blended in an amount of 0.3 parts by weight with 100 parts by weight of polymethylmethacrylate (PMMA, Sumitomo Chemical SUMIPEX), and kneaded by an extruder at an extrusion temperature of 200° C. to produce a near-infrared absorbent PMMA pellet. During the kneading, types and amounts of evolving gases were determined using a gas detection tube.

Evaluation results of Examples 33 to 36 and Comparative Examples. 1 and 2 are shown in Table 2.

TABLE 2

Types and amounts of gases generated in kneading

| | Amine compound | Hydrogen sulfide | Benzene compound |
|---|---|---|---|
| Example 33 | <2 ppm | 0 ppm | <3 ppm |
| Example 34 | <1 ppm | 0 ppm | <3 ppm |
| Example 35 | <2 ppm | 0 ppm | <3 ppm |
| Example 36 | <2 ppm | 0 ppm | <3 ppm |
| Comparative Example 1 | 7 ppm | 50 ppm | >60 ppm |
| Comparative Example 2 | 10 ppm | 60 ppm | >60 ppm |

As can be seen from Table 2, when molding is carried out using the near-infrared absorbent compositions according to the present invention, in effect no generation of malodorous gases was noted.

EXAMPLE 37

A composition comprising compound A-23 and copper β-acryloyloxypropylhydrogenphthalate, mixed in a molar ratio of 1:1, was added in an amount of 0.3 parts by weight to 100 parts by weight of methylmethacrylate to therein. The solution was mixed with 0.15 parts of 2,2'-azo-bis-isobutyronitrile as a polymerization catalyst, injected into a mold comprising a gasket inserted between two parallel glass plates, immersed in a water bath at 60° C. for 3 hours, then heated in an air oven at 90° C. to complete polymerization. After cooling the resin plate was removed from the glass plates to obtain a 3.05 mm thick resin plate.

The resulting resin plate was measured for transmission spectrum at 240 nm to 2,500 nm in wavelength by means of a recording spectrophotometer (Shimadzu UV-3100 and a multi-purpose large-sized sample chamber MPC-3100 incorporated with an integration sphere). The result is shown as A in FIG. 1. For comparison, B in the same Figure is a transmission spectrum of a 3 mm thick ordinary methacrylic resin plate (Sumitomo Chemical). As can be seen from comparison of A and B in the Figure, the resin plate containing the near-infrared absorbent of the present invention well passes light of the visible region, and is superior in absorption properties which cannot be obtained with conventional methacrylic resin.

EXAMPLE 38

Figure 2:
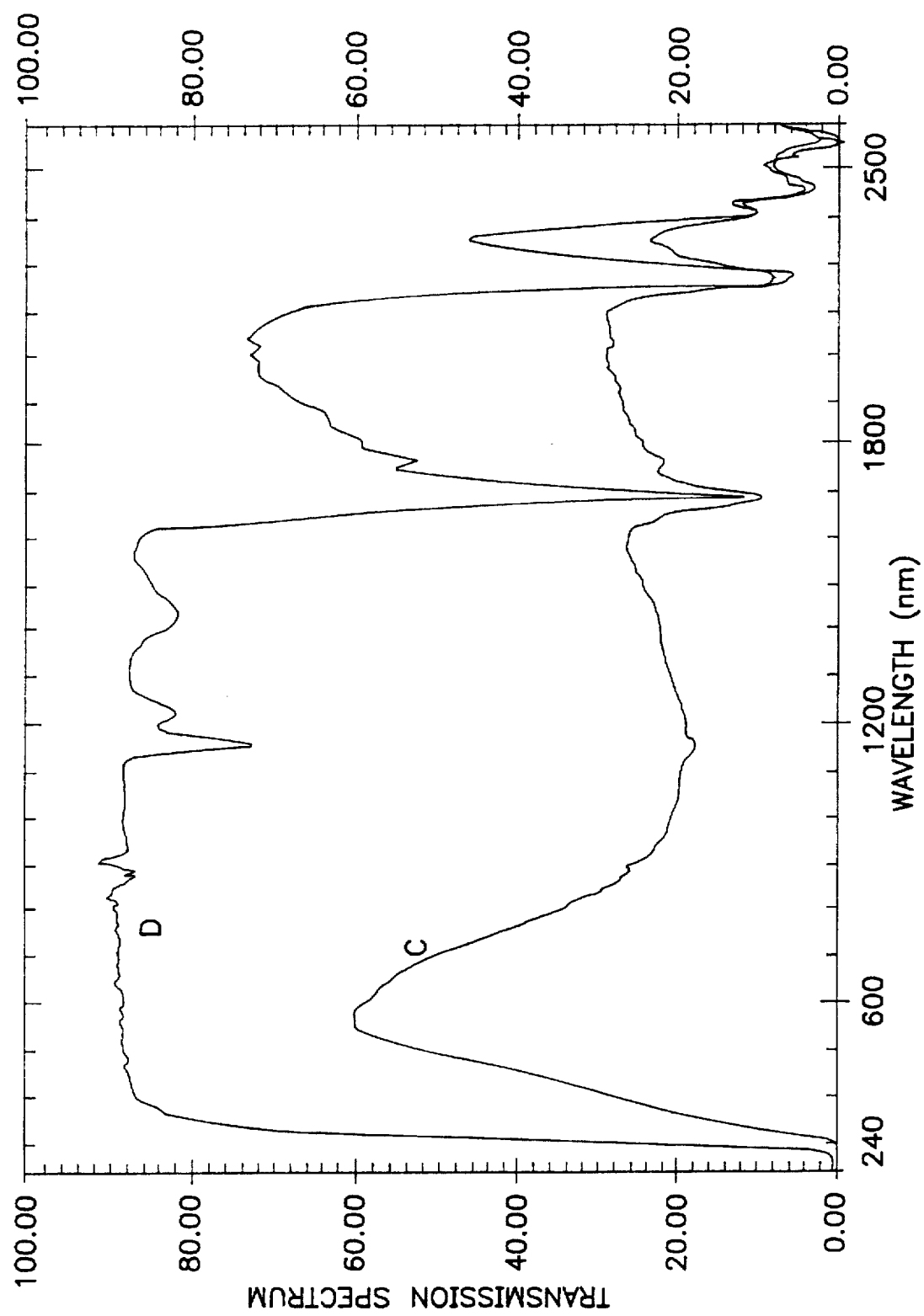
FIG. 2-C: A transmission spectrum of a 2 mm thick PS plate obtained in Example 38.

The near-infrared absorbent PS pellet prepared in Example 33 was injection molded at an injection molding temperature of 160° C. to produce a 2 mm thick near-infrared absorbent PS plate. As in Example 35, this near-infrared absorbent PS plate and a 2 mm thick ordinary PS plate not containing a near-infrared absorbent were measured for transmission spectra at 240 nm to 2,500 nm in wavelength. The results are shown as C and D in FIG. 2. As can be seen from comparison of spectra C and D, the inventive plate well passes light of the visible region, and is superior in absorption properties which cannot be obtained with conventional styrene resin.

EXAMPLE 39

Figure 3:
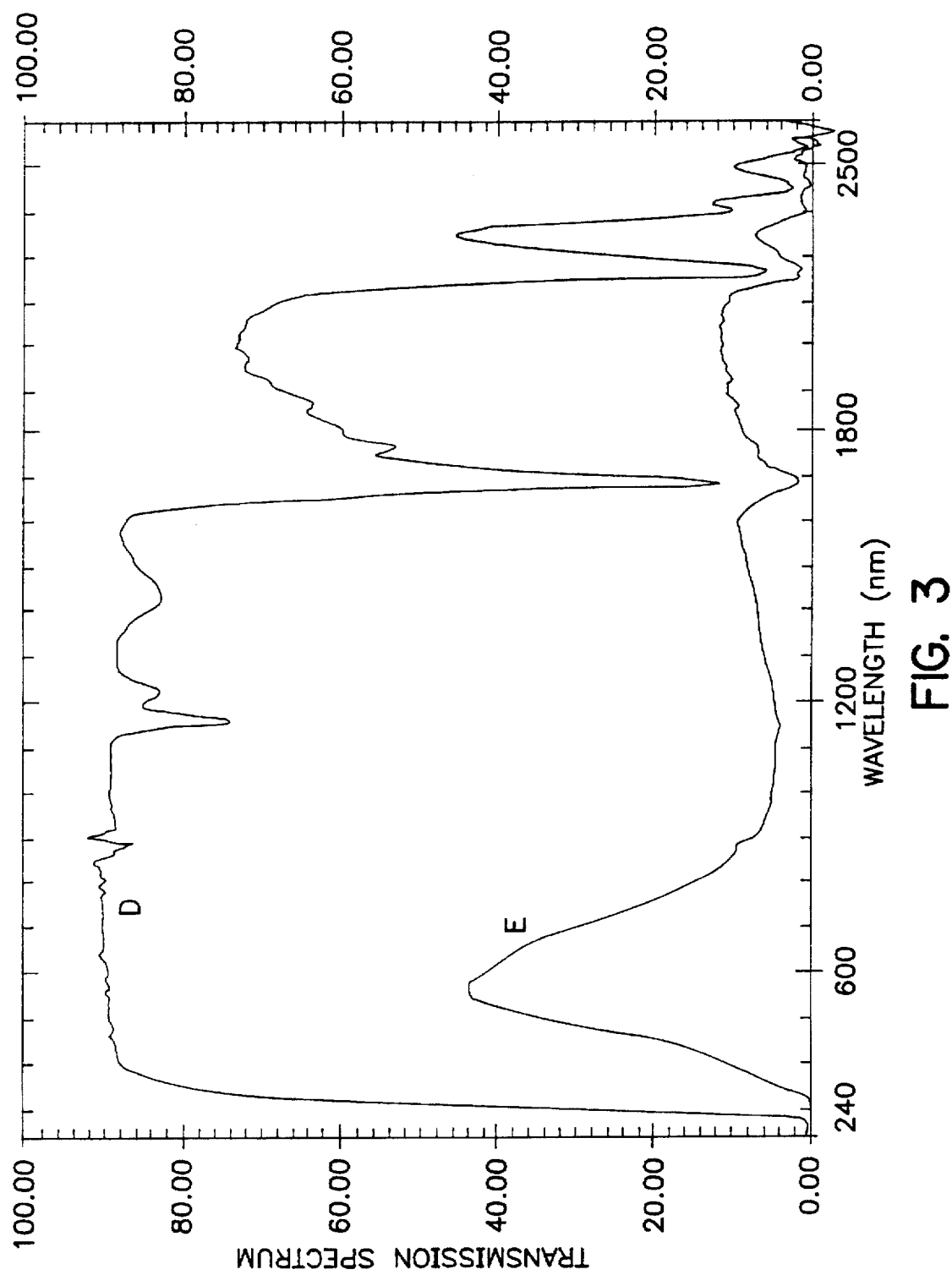
FIG. 3-E: A transmission spectrum of a 2 mm thick PS plate obtained in Example 39.

The near-infrared absorbent PS pellet prepared in Example 34 was injection molded at an injection molding temperature of 160° C. to produce a 2 mm thick near-infrared absorbent PS plate. As in Example 38, the plate was measured for transmission spectrum. The result is shown as spectrum E in FIG. 3. Also shown in FIG. 3 is the transmission spectrum D of a 2 mm thick ordinary PS plate not containing a near-infrared absorbent, from which a similar comparison between the spectra E and D can be made as between spectra C and D in Example 38.

EXAMPLE 40

The near-infrared absorbent PMMA pellet prepared in Example 35 was injection molded at an injection molding temperature of 190° C. to produce a 2 mm thick near-infrared absorbent PMMA plate. As in Example 38, the plate was measured for transmission spectrum. The result is shown as transmission spectrum F in FIG. 4. A 1 mm thick ordinary PMMA plate not containing a near-infrared absorbent was also measured for transmission spectra at 20 nm to 2500 nm in wavelength. The result is shown as transmission spectrum G in FIG. 4. The differences in transmission spectra are readily apparent.

EXAMPLE 41

Figure 4:
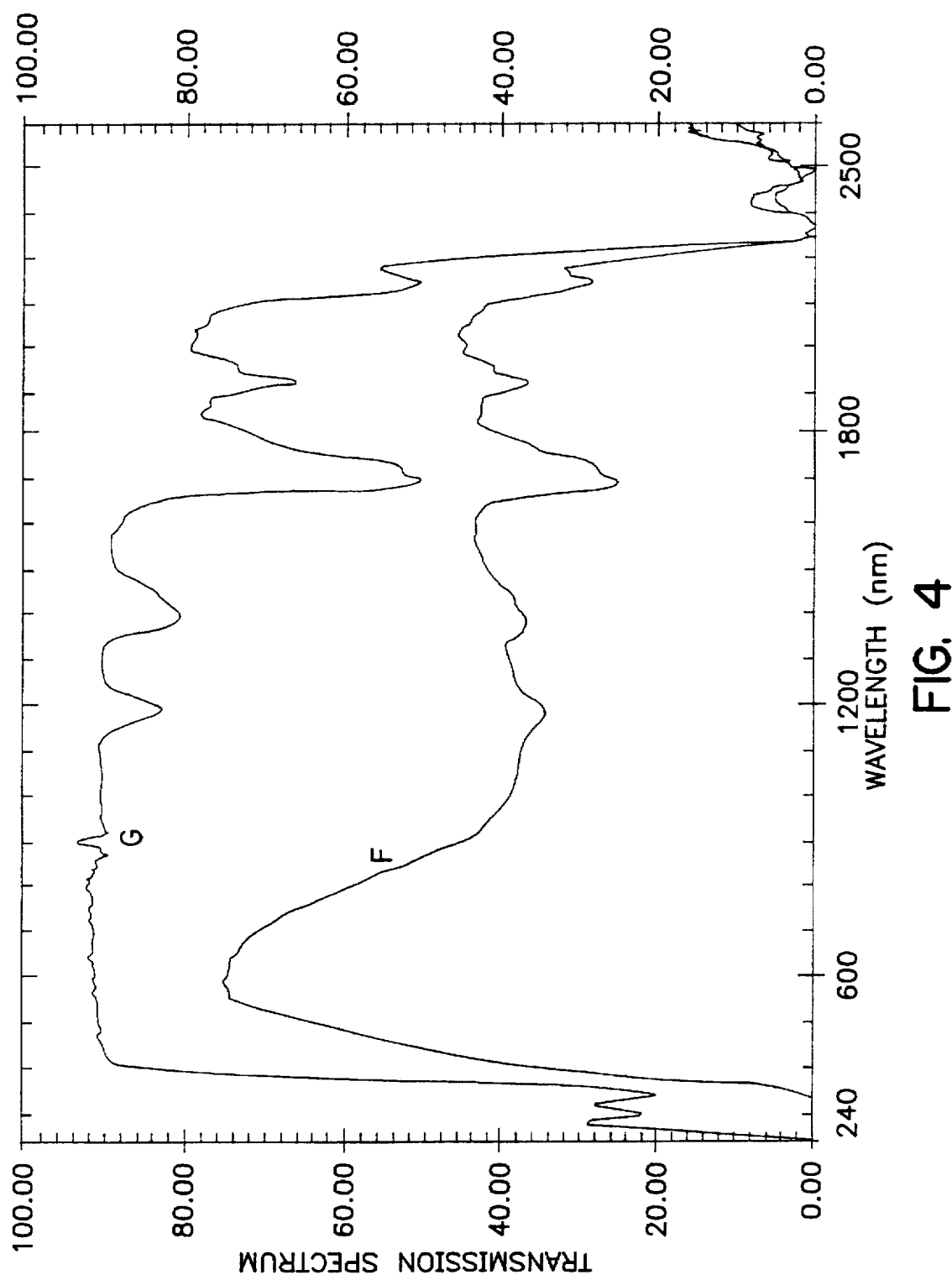
FIG. 4-F: A transmission spectrum of a 1 mm thick PMMA plate obtained in Example 40.
Figure 5:
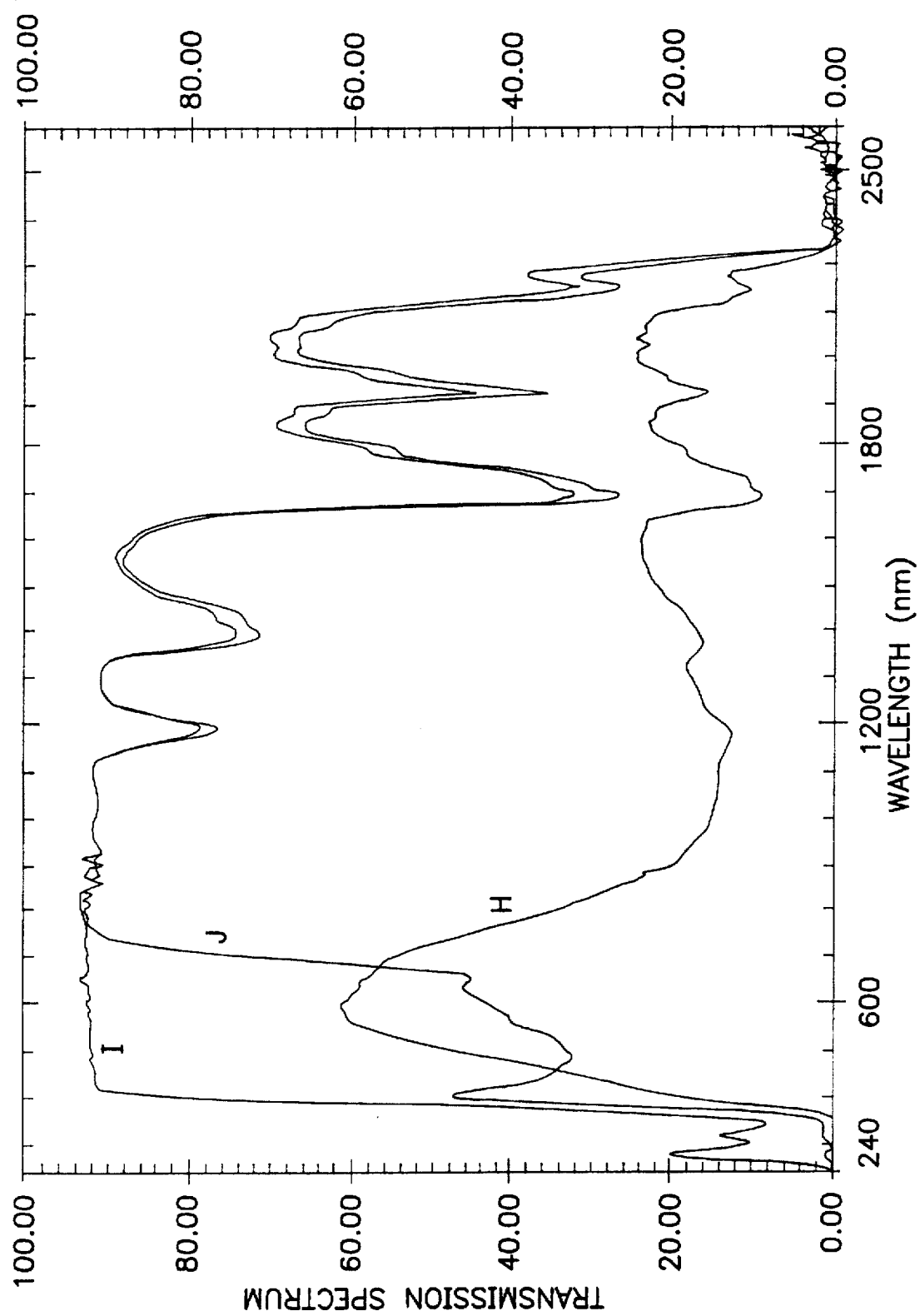
FIG. 5-H: A transmission spectrum of a 2 mm thick PMMA plate obtained in Example 41.

The near-infrared absorbent PMMA pellet prepared in Example 36 was injection molded at an injection molding temperature of 190° C. to produce a 2 mm thick near-infrared absorbent PMMA plate. As in Example 38, the 2 mm thick plate was measured for transmission spectrum. The result is shown as spectra H in FIG. 5. Also shown in FIG. 4 are the transmission spectrum I of an ordinary 2 mm thick PMMA plate without a near-infrared absorbent and the transmission spectrum J of a brown-colored 2 mm thick PMMA plate. The differences in the spectra I and J from spectrum H are readily apparent.

EXAMPLE 42

Figure 6:
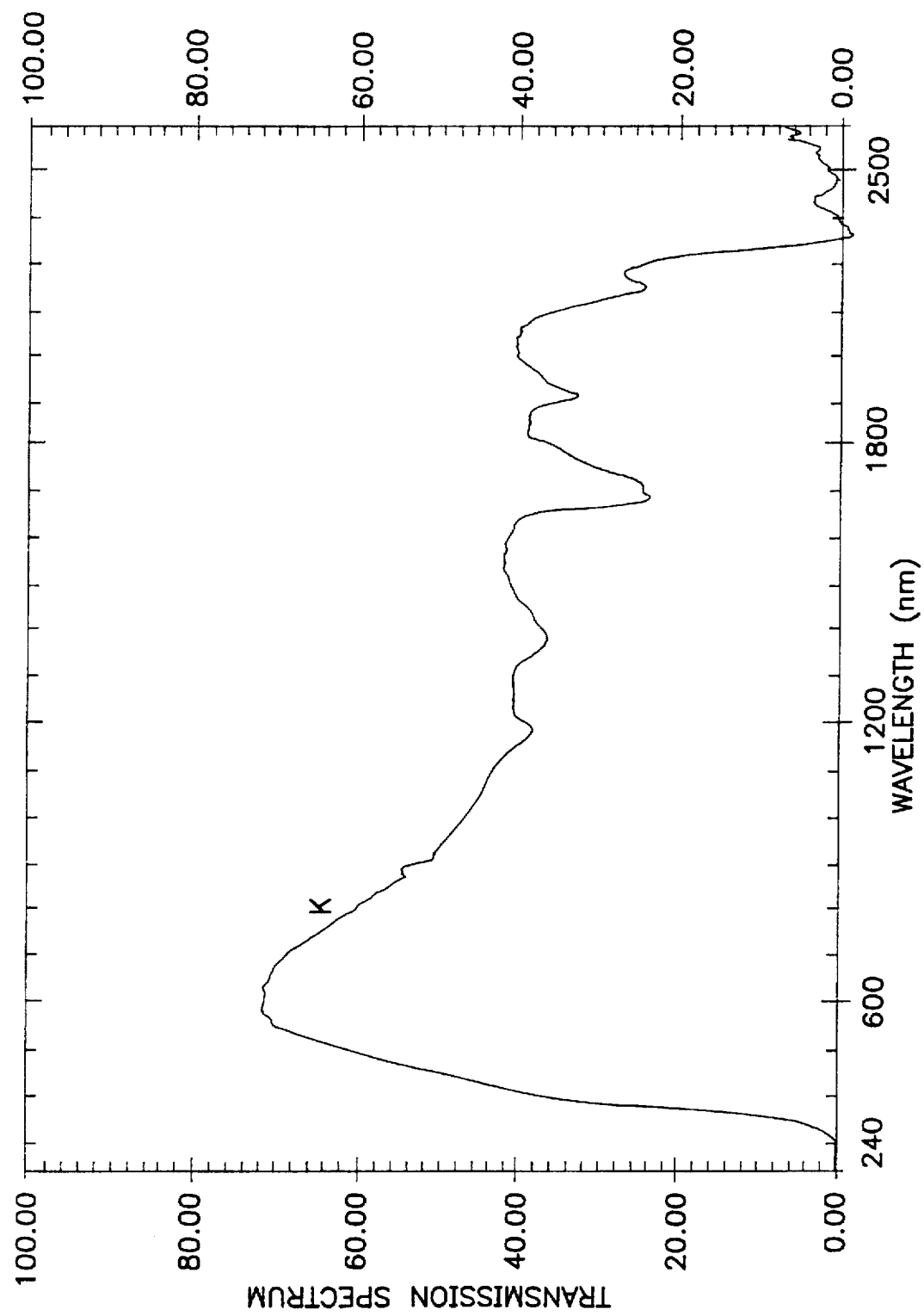
FIG. 6-K: A transmission spectrum of a 2 mm thick PMMA plate obtained in Example 42.

A composition comprising compound A-21 and copper stearate, mixed in a molar ratio of 1:1, was dry blended in an amount of 0.1 part by weight with 100 parts by weight of polymethylmethacrylate (PMMA, Sumitomo Chemical SUMIPEX), and kneaded by an extruder at an extrusion temperature of 200° C. to produce a near-infrared absorbent PMMA pellet. Further, the pellet was injection molded at an injection molding temperature of 190° C. to produce a 2 mm thick near-infrared absorbent PMMA plate. As in Example 38, the plate was measured for transmission spectrum. The result is shown in FIG. 6 as spectrum K.

EXAMPLE 43

Figure 7:
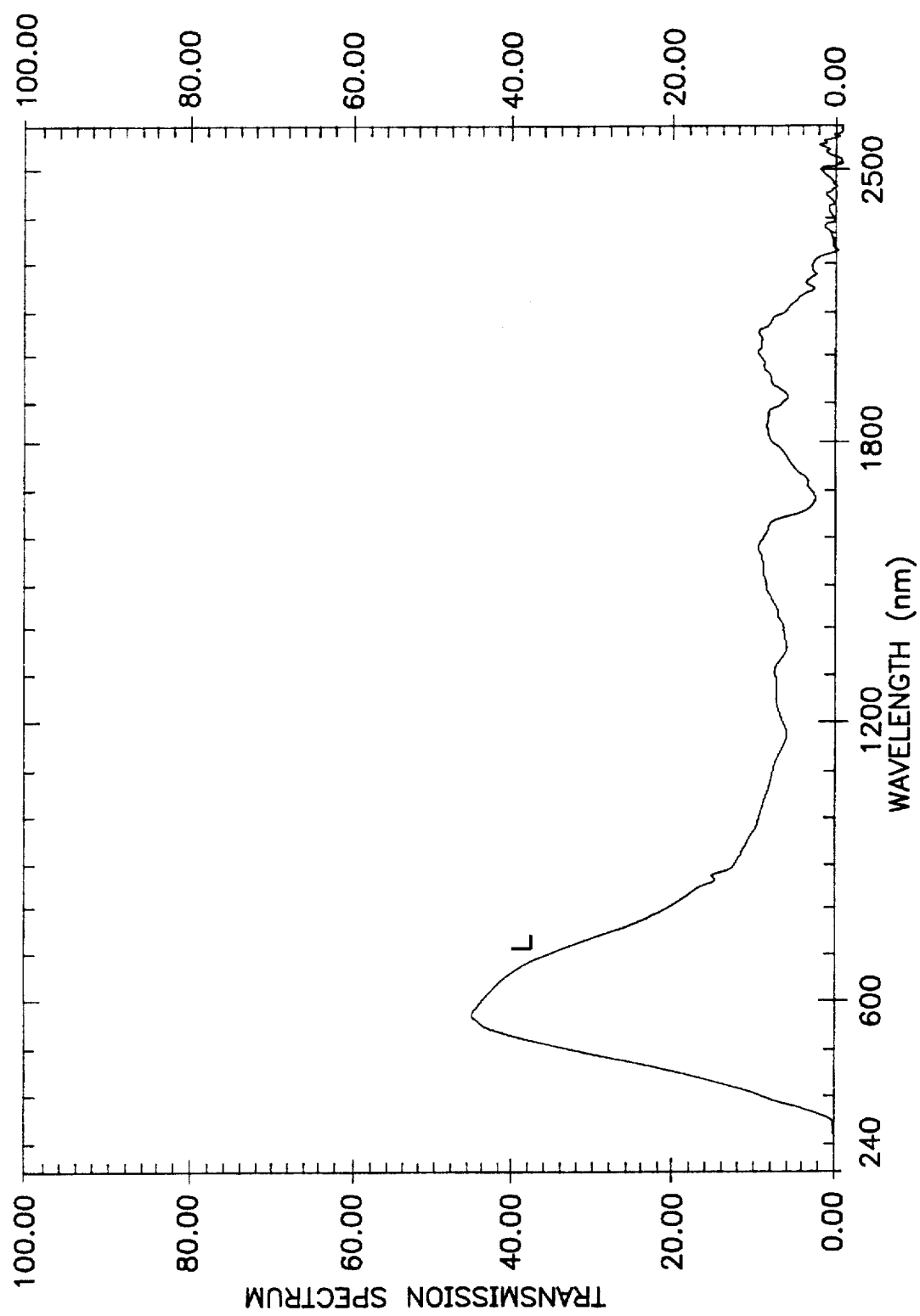
FIG. 7-L: A transmission spectrum of a 2 mm thick PMMA plate obtained in Example 43.

A composition comprising compound A-28 and copper stearate, mixed in a molar ratio of 2:1, was dry blended in an amount of 1 part by weight with 100 parts by weight of polymethylmethacrylate (PMMA, Sumitomo Chemical SUMIPEX), and kneaded by an extruder at an extrusion temperature of 200° C. to produce a near-infrared absorbent PMMA pellet. Further, the pellet was injection molded at an injection molding temperature of 190° C. to produce a 2 mm thick near-infrared absorbent PMMA plate. As in Example 38, the plate was measured for transmission spectrum. The result is shown in FIG. 7 as spectrum L.

COMPARATIVE EXAMPLE 3

A polystyrene (PS, Nippon Steel Chemical ESTYRENE) pellet was injection molded at an injection molding temperature of 160° C. to produce a 2 mm thick PS plate. As in Example 36, the plate was measured for transmission spectrum.

COMPARATIVE EXAMPLE 4

A polymethylmethacrylate (PMMA, Sumitomo Chemical SUMIPEX) bead was kneaded by an extruder at a temperature of 200° C. to produce a pellet. The PMMA pellet was injection molded at an injection molding temperature of 190° C. to produce a 2 mm thick PMMA plate. As in Example 36, the plate was measured for transmission spectrum.

COMPARATIVE EXAMPLE 5

A commercial brown-colored smoke type polymethylmethacrylate plate was measured for transmission spectrum as in Example 36.

From transmission spectra measured in Examples 38 to 43 and Comparative Examples 3 to 5, sunlight transmittances and visible light transmittances were calculated by a method specified in JIS R 3106, and heat wave shielding efficiencies were determined according to Formula [A]. The results are shown in Table 3.

TABLE 3

Sunlight transmittance, visible light transmittance, and heat wave shielding efficiency of plate

|  | Amount (part) | Sunlight transmittance Y | Visible light transmittance E | Heat wave shielding efficiency η |
|---|---|---|---|---|
| Ex. 38 | 0.25 | 31.385 | 48.912 | 35.05 |
| Ex. 39 | 0.5 | 18.126 | 37.285 | 38.32 |
| Ex. 40 | 0.3 | 39.026 | 60.069 | 42.09 |
| Ex. 41 | 0.4 | 16.120 | 34.822 | 37.40 |
| Ex. 42 | 0.15 | 35.581 | 57.516 | 43.87 |
| Ex. 43 | 0.75 | 17.870 | 36.851 | 37.96 |
| Comp. Ex. 3 | — | 86.338 | 89.805 | 6.93 |
| Comp. Ex. 4 | — | 88.696 | 92.011 | 6.63 |
| Comp. Ex. 5 | — | 66.232 | 39.270 | −53.92 |

As can be seen from Table 3, the plate containing the near-infrared absorbent comprising the dimerized thiourea derivative of the present invention and the copper compound showed a heat wave shielding efficiency of about 40%, whereas that containing no near-infrared absorbent had a heat wave shielding efficiency of only about 5%. Further, the commercial heat wave shielding plate had a heat wave shielding efficiency of −53%. As can be seen from the transmission spectra in FIG. 5, the brown-colored plate, which does not absorb near-infrared rays of over 800 nm, merely absorbs visible light to reduce the visible light transmittance, thereby reducing the sunlight transmittance as a whole. Therefore, the heat wave shielding efficiency is a negative value. Thus, the heat wave shielding material using the near-infrared absorbent of the present invention is much superior.

A near-infrared absorbent property appears by mixing and heating a thiourea compound and a copper compound,

37 however, since the dimerized thiourea derivative of the present invention is higher in thermal decomposition temperature than conventional thiourea compounds, it does not decompose when the near-infrared absorbent composition comprising the dimerized thiourea derivative and the copper compound is kneaded with a resin, thereby suppressing generation of malodorous gases.

As described above, the heat wave shielding material formed by mixing the near-infrared absorbent composition with a transparent resin and molding can be used for roofing, window materials, and the like of carport, sunroom, and terrace to suppress temperature increase in the room.

Further, the heat wave shielding material of the present invention passes visible light relatively well and absorbs near-infrared rays in a wide range, and it can also efficiently absorb ultraviolet light as well.

What is claimed is:

1. A near-infrared absorbent composition comprising a dimerized thiourea derivative of Formula (1) and a copper compound mixed in a molar ratio of from about 8:2 to about 1:2:

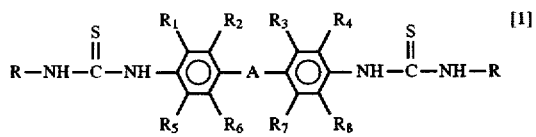

wherein A is $CH_2$, $(CH_2)_2$, S, O, $SO_2$, CONH, NH, or $C(CF_3)_2$; R is an alkyl group having 1 to 18 carbon atoms, a cycloalkyl group having 3 to 18 carbon atoms, an aralkyl group having 7 to 30 carbon atoms, an aryl group having 6 to 30 carbon atoms, an acyl group having 2 to 20 carbon atoms, an alkenyl group having 2 to 20 carbon atoms, or an alkoxycarbonyl group having 2 to 20 carbon atoms; $R_1$, $R_2$, $R_3$, $R_4$, $R_5$, $R_6$, $R_7$ and $R_8$ are each independently a lower alkyl group having 1 to 6 carbon atoms, nitro group, cyano group, halogen atom, or hydrogen atom.

2. A near-infrared absorbent obtained by heating the near-infrared absorbent composition of claim 1.

3. A resin composition comprising 0.05 to 5 parts by weight of the near-infrared absorbent composition of claim 1 and 100 parts by weight of a resin.

4. The resin composition of claim 3 wherein said resin is a (meth)acrylic ester resin.

5. A near-infrared absorbent hard-coating agent comprising the near-infrared absorbent composition of claim 1 mixed in a ratio of 5 to 50 parts by weight with 100 parts by weight based on total solid content of a silicone hard-coating agent.

6. A heat wave shielding material obtained by heat molding the near-infrared absorbent resin composition of claim 3.

7. A heat wave shielding material having a coating layer comprising the near-infrared absorbent resin composition of claim 3 provided on the surface of a transparent substrate.

8. A method of producing a near-infrared absorbent resin composition or a near-infrared absorbent molding comprising the steps of: mixing 0.1 to 1.5 parts by weight of the near-infrared absorbent composition of claim 1 with 100 parts by weight of a polymerizable raw material, and heat polymerizing in the presence of an azo compound radical polymerization initiator.

9. The method of claim 8 wherein said polymerizable raw material is an unsaturated monomer comprising a (meth) acrylic ester monomer and polymer thereof.

10. A near-infrared absorbent composition comprising a dimerized thiourea derivative of Formula (2) and a copper compound mixed in a molar ratio of from about 8:2 to about 1:2:

38

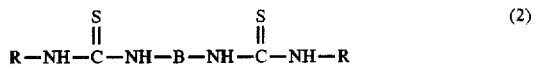

wherein R is an alkyl group having 1 to 18 carbon atoms, a cycloalkyl group having 3 to 18 carbon atoms, an aralkyl group having 7 to 30 carbon atoms, an aryl group having 6 to 30 carbon atoms, or an alkenyl group having 2 to 20 carbon atoms, and B is a phenyl group, naphthyl group, biphenyl group.

11. A heat wave shielding material obtained by heat molding the near-infrared absorbent resin composition of claim 4.

12. A heat wave shielding material having a coating layer comprising the near-infrared absorbent resin composition of claim 4 provided on the surface of a transparent substrate.

13. A heat wave shielding material having a coating layer comprising the near-infrared absorbent hard-coating agent of claim 5 provided on the surface of a transparent material.

14. A resin composition comprising 0.05 to 5 parts by weight of the near-infrared absorbent of claim 2 and 100 parts by weight of a resin.

15. The resin composition of claim 14 wherein said resin is a (meth)acrylic ester resin.

16. A near-infrared absorbent hard-coating agent comprising the near-infrared absorbent of claim 2 mixed in a ratio of 5 to 50 parts by weight with 100 parts by weight based on total solid content of silicone hard-coating agent.

17. The near-infrared absorbent composition according to claim 1, wherein the copper compound is copper bis-acetylacetonate, copper hydroxide, or a compound of Formula $(Y-Z)_m Cu$, wherein Y represents an alkyl group, cycloalkyl group or aryl group and Z represents COO, $SO_4$, $SO_3$, $PO_4$, and m is an integer of from 1 to 4.

18. The near-infrared absorbent composition according to claim 1, wherein the copper compound is selected from the group consisting of copper stearate, copper palmitate, copper oleate, copper behenate, copper laurate, copper caprate, copper caprylate, copper caproate, copper valerate, copper isobutyrate, copper 4-cyclohexylbutyrate, copper butyrate, copper propionate, copper acetate, copper formate, copper benzoate, copper toluate, copper t-butylbenzoate, copper chlorobenzoate, copper dichlorobenzoate, copper trichlorobenzoate, copper bromobenzoate, copper iodobenzoate, copper phenylbenzoate, copper benzoylbenzoate, copper nitrobenzoate, copper aminobenzoate, copper oxalate, copper malonate, copper succinate, copper glutarate, copper adipate, copper pimelate, copper suberate, copper azelaate, copper sebacate, copper citrate, copper phthalate, copper monoalkylester phthalate, copper monoacryloylester phthalate, copper naphthenate, copper naphthalenecarboxylate, copper diphenylamine-2-carboxylate, copper tartarate, copper gluconate, copper octylate, copper benzenesulfonate, copper p-toluenesulfonate, copper 2,5-dimethylbenzenesulfonate, copper 2-methoxycarbonyl- 5-methylsulfonate, copper dodecylbenzenesulfonate, copper naphthalenesulfonate, copper aminonaphthalenesulfonate, copper dodecylsulfate, copper α-naphthylphosphate, copper stearylphosphate, copper laurylphosphate, copper di-2-ethylhexylphosphate, and copper isodecylphosphate.

19. The near-infrared absorbent composition of claim 1 wherein, in the definition of R, said aryl group is unsubstituted or is substituted by from 1 to 3 halogen atoms or alkyl groups of 1 to 6 carbon atoms.

20. A dimerized thiourea derivative selected from the group consisting of

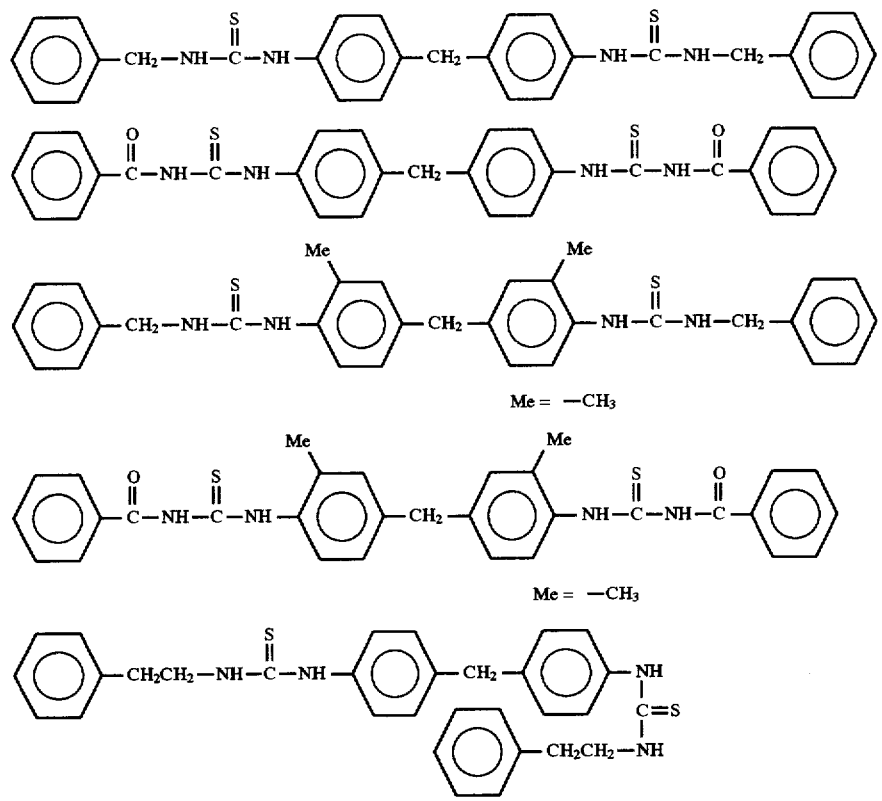
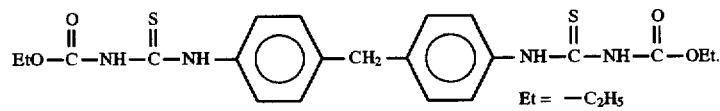
21. A dimerized thiourea derivative selected from the group consisting of
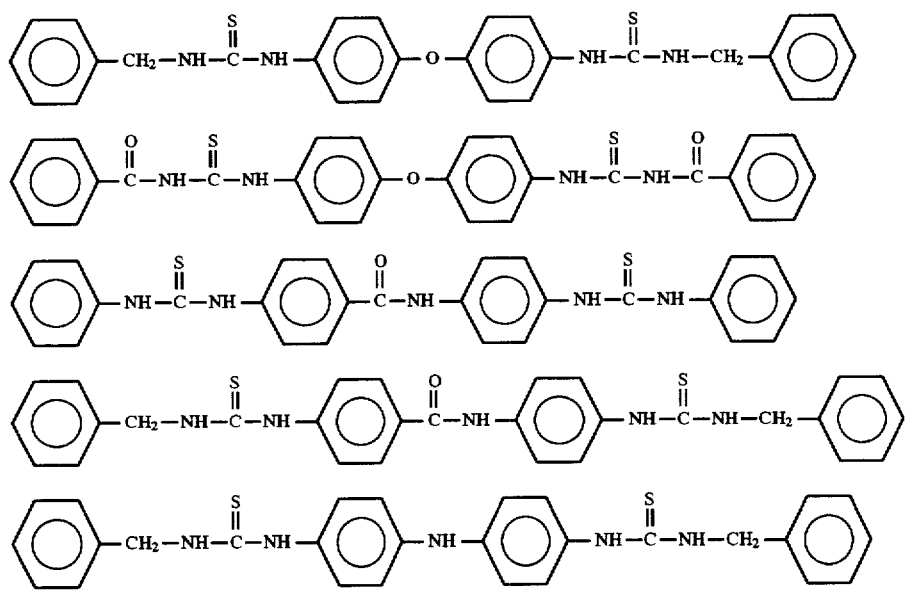

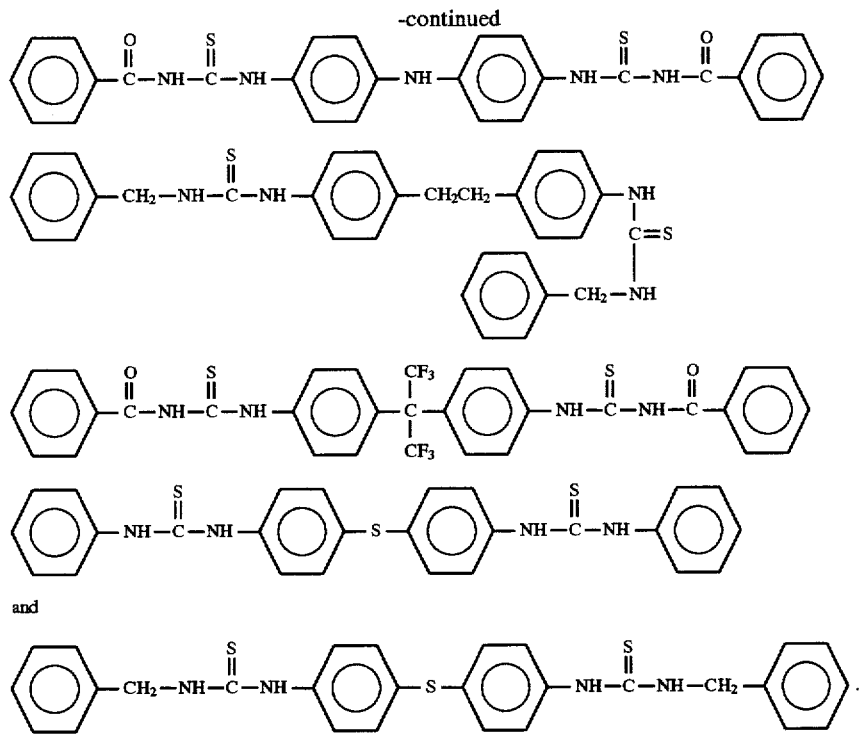

and

22. A near-infrared absorbent obtained by heating the near-infrared absorbent composition of claim 10.

23. A resin composition comprising 0.05 to 5 parts by weight of the near-infrared absorbent composition of claim 10 and 100 parts by weight of a resin.

24. The resin composition of claim 23 wherein said resin is a (meth)acrylic ester resin.

25. A near-infrared absorbent hard-coating agent comprising the near-infrared absorbent composition of claim 10 mixed in a ratio of 5 to 50 parts by weight with 100 parts by weight based on total solid content of a silicone hard-coating agent.

26. A heat wave shielding material obtained by heat molding the near-infrared absorbent resin composition of claim 25.

27. A heat wave shielding material having a coating layer comprising the near-infrared absorbent resin composition of claim 25 provided on the surface of a transparent substrate.

28. A method of producing a near infrared absorbent resin composition or a near infrared absorbent comprising the steps of: mixing 0.1 to 1.5 parts by weight of the near-infrared absorbent composition of claim 10 with 100 parts by weight of a polymerizable raw material, and heat polymerizing in the presence of azo compound radical polymerization initiator.

29. The method of claim 28 wherein said polymerizable raw material is as unsaturated monomer comprising a (meth)acrylic ester monomer and polymer thereof.

30. A dimerized thiourea derivative of formula (12)

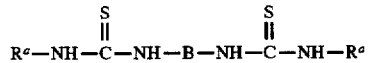
(12)

wherein $R^a$ is an acyl group having 2 to 20 carbon atoms, and B is a 1,3-phenyl group, 1,4-phenyl group, naphthyl group or biphenyl group.

31. The near-infrared absorbent composition according to claim 10, wherein the copper compound is selected from the group consisting of copper stearate, copper palmitate, copper oleate, copper behenate, copper laurate, copper caprate, copper caprylate, copper caproate, copper valerate, copper isobutyrate, copper 4-cyclohexyl butyrate, copper butyrate, copper propionate, copper acetate, copper formate, copper benzoate, copper toluate, copper t-butylbenzoate, copper chlorobenzoate, copper dichlorobenzoate, copper trichlorobenzoate, copperbromo-benzoate, copper iodobenzoate, copper phenylbenzoate, copper benzoylbenzoate, copper nitrobenzoate, copper aminobenzoate, copper oxalate, copper malonate, copper succinate, copper glutarate, copper adipate, copper pimelate, copper suberate, copper azelaate, copper sebacate, copper citrate, copper phthalate, copper monoalkylester phthalate, copper monoacryloyester phthalate, copper naphthenate, copper naphthalaenecarboxylate, copper diphenylamine-2-carboxylate, copper tartarate, copper gluconate, copper octylate, copper benzenesulfonate, copper p-toluenesulfonate, copper 2,5-dimethylbenzensulfonate, copper 2-methoxy-carbonyl-5-methylsulfonate, copper dodecylbenzenesulfonate, copper naphthalenesulfonate, copper aminonaphthalenesulfonate, copper dodecylsulfate, copper α-naphthylphosphate, copper stearylphosphate, copper laurylphosphate, copper di-2-ethylhexylphosphate, and copper isodecylphosphate.

32. A dimerized thiourea derivative which is selected from the group consisting of

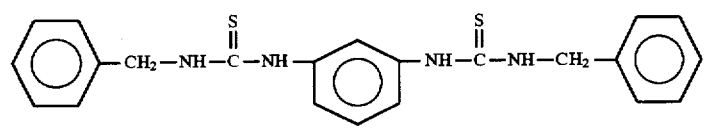
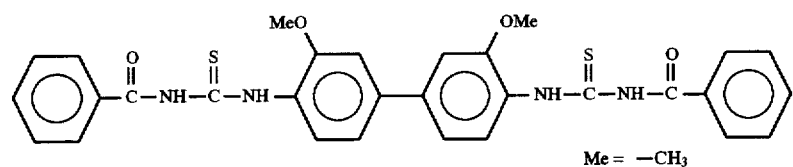
Me = —CH₃
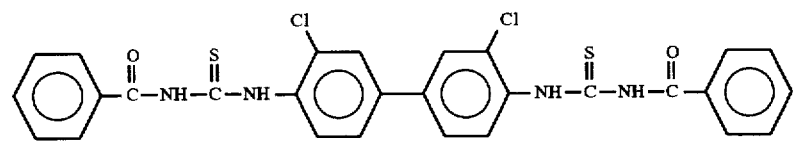
and
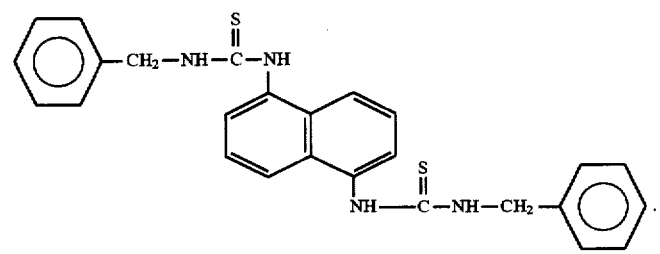
* * * * *